United States Patent
Dziura et al.

(10) Patent No.: US 9,310,296 B2
(45) Date of Patent: Apr. 12, 2016

(54) OPTIMIZING AN OPTICAL PARAMETRIC MODEL FOR STRUCTURAL ANALYSIS USING OPTICAL CRITICAL DIMENSION (OCD) METROLOGY

(75) Inventors: Thaddeus G. Dziura, San Jose, CA (US); Yung-Ho Chuang, Cupertino, CA (US); Bin-ming Benjamin Tsai, Saratoga, CA (US); Xuefeng Liu, San Jose, CA (US); John J. Hench, San Jose, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 1256 days.

(21) Appl. No.: 13/164,398

(22) Filed: Jun. 20, 2011

(65) Prior Publication Data

US 2012/0323356 A1    Dec. 20, 2012

(51) Int. Cl.
*G05B 13/00* (2006.01)
*G01N 21/47* (2006.01)
*G01B 11/24* (2006.01)
*G03F 7/20* (2006.01)
(Continued)

(52) U.S. Cl.
CPC ............... *G01N 21/47* (2013.01); *G01B 11/24* (2013.01); *G01N 21/956* (2013.01); *G03F 7/70625* (2013.01); *G01B 2210/56* (2013.01); *G01N 2021/95615* (2013.01); *G06F 17/5009* (2013.01)

(58) Field of Classification Search
CPC ............... G01N 21/47; G01N 21/956; G01N 2021/95615; G03F 7/70625; G01B 11/24; G01B 2210/56; G06F 17/5009

USPC .............................................. 700/121; 703/2
See application file for complete search history.

(56) References Cited

U.S. PATENT DOCUMENTS

| 7,355,728 | B2 | 4/2008 | Li et al. | |
|---|---|---|---|---|
| 8,798,966 | B1 * | 8/2014 | Hench et al. | 703/2 |
| 2002/0149774 | A1 * | 10/2002 | McAninch | 356/445 |

(Continued)

FOREIGN PATENT DOCUMENTS

EP    1037012    9/2000

OTHER PUBLICATIONS

International Preliminary Report on Patentability dated Dec. 23, 2013, in International Patent Application No. PCT/US2012/042437.

(Continued)

*Primary Examiner* — Mohammad Ali
*Assistant Examiner* — Ziaul Karim
(74) *Attorney, Agent, or Firm* — Blakely Sokoloff Taylor & Zapman

(57) ABSTRACT

Optimization of optical parametric models for structural analysis using optical critical dimension metrology is described. A method includes determining a first optical model fit for a parameter of a structure. The first optical model fit is based on a domain of quantities for a first model of the structure. A first near optical field response is determined for a first quantity of the domain of quantities and a second near optical field response is determined for a second, different quantity of the domain of quantities. The first and second near optical field responses are compared to locate a common region of high optical field intensity for the parameter of the structure. The first model of the structure is modified to provide a second, different model of the structure. A second, different optical model fit is determined for the parameter of the structure based on the second model of the structure.

24 Claims, 22 Drawing Sheets

(51) Int. Cl.
*G01N 21/956* (2006.01)
*G06F 17/50* (2006.01)

(56) References Cited

U.S. PATENT DOCUMENTS

2004/0122599 A1 6/2004 Opsal et al.
2004/0265477 A1 12/2004 Nabatova-Gabain et al.
2006/0033921 A1* 2/2006 Den Boef et al. ............ 356/446

OTHER PUBLICATIONS

International Search Report and Written Opinion of the International Searching Authority dated Jan. 2, 2013, in International Patent Application No. PCT/US2012/042437.

Taiwan Office Action dated Jan. 8, 2016, in Taiwan Application No. 101121678, 6 pages.

* cited by examiner

OPTIMIZING AN OPTICAL PARAMETRIC MODEL FOR STRUCTURAL ANALYSIS USING OPTICAL CRITICAL DIMENSION (OCD) METROLOGY

TECHNICAL FIELD

Embodiments of the present invention are in the field of optical metrology, and, more particularly, relate to methods of optimizing optical parametric models for structural analysis using optical critical dimension (OCD) metrology.

BACKGROUND

For the past several years, a rigorous couple wave approach (RCWA) and similar algorithms have been widely used for the study and design of diffraction structures. In the RCWA approach, the profiles of periodic structures are approximated by a given number of sufficiently thin planar grating slabs. Specifically, RCWA involves three main operations, namely, the Fourier expansion of the field inside the grating, calculation of the eigenvalues and eigenvectors of a constant coefficient matrix that characterizes the diffracted signal, and solution of a linear system deduced from the boundary matching conditions. RCWA divides the problem into three distinct spatial regions: (1) the ambient region supporting the incident plane wave field and a summation over all reflected diffracted orders, (2) the grating structure and underlying non-patterned layers in which the wave field is treated as a superposition of modes associated with each diffracted order, and (3) the substrate containing the transmitted wave field.

The accuracy of the RCWA solution depends, in part, on the number of terms retained in the space-harmonic expansion of the wave fields, with conservation of energy being satisfied in general. The number of terms retained is a function of the number of diffraction orders considered during the calculations. Efficient generation of a simulated diffraction signal for a given hypothetical profile involves selection of the optimal set of diffraction orders at each wavelength for both transverse-magnetic (TM) and/or transverse-electric (TE) components of the diffraction signal. Mathematically, the more diffraction orders selected, the more accurate the simulations. However, the higher the number of diffraction orders, the more computation is required for calculating the simulated diffraction signal. Moreover, the computation time is a nonlinear function of the number of orders used.

The input to the RCWA calculation is a profile or model of the periodic structure. In some cases cross-sectional electron micrographs are available (from, for example, a scanning electron microscope or a transmission electron microscope). When available, such images can be used to guide the construction of the model. However a wafer cannot be cross sectioned until all desired processing operations have been completed, which may take many days or weeks, depending on the number of subsequent processing operations. Even after all the desired processing operations are complete, the process to generate cross sectional images can take many hours to a few days because of the many operations involved in sample preparation and in finding the right location to image. Furthermore the cross section process is expensive because of the time, skilled labor and sophisticated equipment needed, and it destroys the wafer.

Thus, there is a need for a method for efficiently generating an accurate model of a periodic structure given limited information about that structure, a method for optimizing the parameterization of that structure and a method of optimizing the measurement of that structure.

SUMMARY

Embodiments of the present invention include methods of optimizing an optical parametric model of a structure to be measured using optical critical dimension (OCD) metrology. Other embodiments include methods of optimizing the parameterization of an optical model of a structure. Other embodiments also include methods of developing a measurement recipe and/or developing a library for optical critical dimensions metrology of a structure. Further embodiments include an optical metrology apparatus that incorporates one, or more, of the methods disclosed herein.

In an embodiment, a method of optimizing optical parametric models for structural analysis using OCD metrology includes determining a first optical model fit for a parameter of a structure. The first optical model fit is based on a domain of quantities for a first model of the structure. A first near optical field response is determined for a first quantity of the domain of quantities and a second near optical field response is determined for a second, different quantity of the domain of quantities. The first and second near optical field responses are compared to locate a common region of high optical field intensity for the parameter of the structure. The first model of the structure is modified to provide a second, different model of the structure. A second, different optical model fit is determined for the parameter of the structure based on the second model of the structure. In one embodiment, the domain of quantities is a domain such as, but not limited to, a domain of wavelengths, a domain of angles of incidence, a domain of azimuth angles, or a domain of polarization states.

In another embodiment, a method of optimizing optical parametric models for three-dimensional structural analysis using OCD metrology includes determining a first optical model fit for a parameter of a three-dimensional structure. The first optical model fit is based on a domain of wavelengths for a first model of the three-dimensional structure. A first near optical field response is determined for a first wavelength of the domain of wavelengths at a plurality of azimuth angles. A second near optical field response is determined for a second, different wavelength of the domain of wavelengths at one of the plurality of azimuth angles. The first and second near optical field responses are compared to locate a common region of high optical field intensity for the parameter of the three-dimensional structure. The first model of the three-dimensional structure is modified to provide a second, different model of the three-dimensional structure. A second, different optical model fit for the parameter of the three-dimensional structure is determined based on the second model of the three-dimensional structure.

In another embodiment, a method of optimizing optical parametric models for structural analysis using OCD metrology includes determining a first optical model fit for a parameter of a structure. The first optical model fit is based on a domain of wavelengths, angles of incidence, azimuth angles and/or polarization states for a first model of the structure. A first near optical field response is determined for a first combination of a wavelength, an angle of incidence, an azimuth angle and a polarization state of the domain and a second near optical field response is determined for a second, different combination of a wavelength, an angle of incidence, an azimuth angle and a polarization state of the domain. The first and second near optical field responses are compared to locate a common region of high optical field intensity for the parameter of the structure. The first model of the structure is modified to provide a second, different model of the structure. A second, different optical model fit is determined for the parameter of the structure based on the second model of the structure.

In another embodiment, a machine-accessible storage medium has instructions stored thereon which cause a data processing system to perform a method of optimizing optical parametric models for structural analysis using OCD metrology. The method includes determining a first optical model fit for a parameter of a structure. The first optical model fit is based on a domain of wavelengths for a first model of the structure. A first near optical field response is determined for a first wavelength of the domain of wavelengths and a second near optical field response is determined for a second, different wavelength of the domain of wavelengths. The first and second near optical field responses are compared to locate a common region of high optical field intensity for the parameter of the structure. The first model of the structure is modified to provide a second, different model of the structure. A second, different optical model fit is determined for the parameter of the structure based on the second model of the structure.

In another embodiment, a machine-accessible storage medium has instructions stored thereon which cause a data processing system to perform a method of optimizing optical parametric models for three-dimensional structural analysis using OCD metrology. The method includes determining a first optical model fit for a parameter of a three-dimensional structure. The first optical model fit is based on a domain of wavelengths for a first model of the three-dimensional structure. A first near optical field response is determined for a first wavelength of the domain of wavelengths at a plurality of azimuth angles. A second near optical field response is determined for a second, different wavelength of the domain of wavelengths at one of the plurality of azimuth angles. The first and second near optical field responses are compared to locate a common region of high optical field intensity for the parameter of the three-dimensional structure. The first model of the three-dimensional structure is modified to provide a second, different model of the three-dimensional structure. A second, different optical model fit for the parameter of the three-dimensional structure is determined based on the second model of the three-dimensional structure.

In another embodiment, a data processing system with a machine-accessible storage medium is included in an optical metrology system. That optical metrology system may have more than one optical subsystem or operating mode. The machine-accessible storage medium has instructions stored thereon which cause the data processing system to perform a method of optimizing optical parametric models for three-dimensional structural analysis using OCD metrology. The method includes determining a first optical model fit for a parameter of a three-dimensional structure. The first optical model fit is based on a domain of wavelengths, angles of incidence, azimuth angles and polarization states for a first model of the three-dimensional structure. A first near optical field response is determined for a first combination of wavelength, angle of incidence, azimuth angle and polarization state of the domain. A second near optical field response is determined for a second, different combination of wavelength, angle of incidence, azimuth angle and polarization state of the domain. The first and second near optical field responses are compared to locate a region of high optical field intensity for the parameter of the three-dimensional structure. The measuring subsystem or operating mode is selected to improve the sensitivity of the measurement to changes in the parameter by using the subsystem or mode that includes the combination of wavelength, angle of incidence, azimuth angle and polarization state corresponding to the higher optical field intensity.

DETAILED DESCRIPTION

Figure 1:
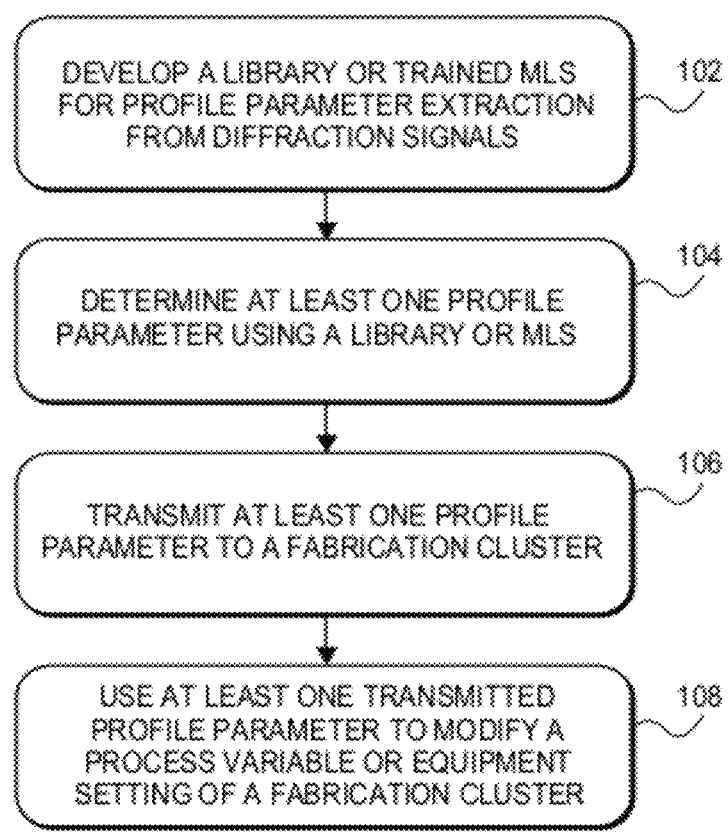
FIG. 1 depicts a flowchart representing an exemplary series of operations for determining and utilizing structural parameters for automated process and equipment control, in accordance with an embodiment of the present invention.

Methods of optimizing optical parametric models for structural analysis using optical critical dimension (OCD) metrology are described herein. In the following description, numerous specific details are set forth, such as examples of specific semiconductor structures, in order to provide a thorough understanding of embodiments of the present invention. It will be apparent to one skilled in the art that embodiments of the present invention may be practiced without these specific details. In other instances, well-known processing operations, such as fabricating stacks of patterned material layers, are not described in detail in order to not unnecessarily obscure embodiments of the present invention. Furthermore, it is to be understood that the various embodiments shown in the figures are illustrative representations and are not necessarily drawn to scale.

Intelligent targeting of parameters and regions for alteration of an optical model may be performed to improve a model spectral fit, as will be described in embodiments herein. By contrast, typically, the applications engineer uses a trial and error method of improving the model fit. The trial and error method involves modification of various regions of an OCD shape model, or various layers in a filmstack model, in their shape or optical dispersion (e.g., index and extinction) characteristics, one region or layer at a time. The model fit quality is then compared to the model fit quality of the original model. The conventional method is terminated when a model change is identified that results in a significant improvement in model fit quality, and reasonable parameter value results are provided.

However, the conventional trial and error method may be very time consuming. For example, typical OCD models may contain twenty or more shape parameters. Any parameters that are fixed in the current (e.g., poorly performing) model have to be floated in a test model. If the test model does not provide a better model fit quality, then various changes to the material index or extinction may have to be considered. In the case that such model changes do not lead to improved results, various shape changes at all significant spatial regions of the model may have to be tested. Such a process may require a duration of days or even weeks, especially for three-dimensional OCD models, where the core computation time per spectrum is typically long.

In accordance with one or more embodiments of the present invention, software that is capable of calculating optical fields for a filmstack or OCD grating is used to compute the near optical field in an immediate region of a structure, such as in an immediate region of a semiconductor device. The calculation of the near optical field may be done using any algorithm capable of calculating solutions to Maxwell's equations for propagation of electromagnetic waves in media. An RCWA algorithm similar to that used to calculate the far (diffracted) optical fields may be utilized to calculate the near optical fields. Alternatively finite element or finite difference methods, volume integral (Green's function) methods or boundary element methods may be used to compute the near optical fields. Since the near optical fields are used to guide the optimization of a parametric structural model, in some cases, high numerical accuracy may not be needed. In such cases, a low truncation order or a coarse grid may be used to speed computation while still making apparent the trends of how, at different locations, the near optical field strength varies with angle, wavelength and polarization.

For a more detailed description of Green's function methods and algorithms as applied to OCD scatterometry, see U.S. Pat. No. 7,038,850, entitled CD METROLOGY ANALYSIS USING GREEN'S FUNCTION, filed on Jan. 6, 2005, which is incorporated herein by reference in its entirety. For a more detailed description finite difference methods and algorithms as applied to OCD scatterometry, see U.S. Pat. No. 7,106,459, entitled CD METROLOGY ANALYSIS USING A FINITE DIFFERENCE METHOD, filed on Jun. 10, 2005, which is incorporated herein by reference in its entirety. Commercial finite element analysis software may also be suitable for calculating the near optical fields. For example, the "COMSOL Multiphysics" software package (COMSOL AB, Stockholm, Sweden) can be used to compute near optical fields in structures.

Methods described herein may be implemented to reduce the time to optimize an OCD shape or film thickness model by quickly identifying the most likely regions of a structure (such as a semiconductor device) that are responsible for poor model fit to experimental data. In an embodiment, one or more approaches described herein may be used to eliminate a significant number of operations otherwise employed in a conventional trial and error methodology. For example, in one embodiment, a method enables an applications engineer to more quickly optimize a parametric model and generate final "good fit" results.

In general, orders of a diffraction signal may be simulated as being derived from a periodic structure. The zeroth order represents a diffracted signal at an angle equal to the angle of incidence of a hypothetical incident beam, with respect to the normal N of the periodic structure. Higher diffraction orders are designated as +1, +2, +3, −1, −2, −3, etc. Other orders known as evanescent orders may also be considered. In accordance with an embodiment of the present invention, a simulated diffraction signal is generated for use in optical metrology. For example, profile parameters, such as structural shape and film thicknesses, may be modeled for use in optical metrology. Optical properties of materials, such as index of refraction and coefficient of extinction, (n & k), in structures may also be modeled for use in optical metrology.

Calculations based simulated diffraction orders may be indicative of profile parameters for a patterned film, such as a patterned semiconductor film or structure based on a stack of films, and may be used for calibrating automated processes or equipment control. FIG. 1 depicts a flowchart 100 representing an exemplary series of operations for determining and utilizing structural parameters, such as profile parameters, for automated process and equipment control, in accordance with an embodiment of the present invention.

Referring to operation 102 of flowchart 100, a library or trained machine learning systems (MLS) is developed to extract profile parameters from a set of measured diffraction signals. In operation 104, at least one profile parameter of a structure is determined using the library or the trained MLS. In operation 106, the at least one profile parameter is transmitted to a fabrication cluster configured to perform a processing operation, where the processing operation may be executed in the semiconductor manufacturing process flow either before or after measurement operation 104 is made. In operation 108, the at least one transmitted profile parameter is used to modify a process variable or equipment setting for the processing operation performed by the fabrication cluster.

For a more detailed description of machine learning systems and algorithms, see U.S. Pat. No. 7,831,528, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. For a description of diffraction order optimization for two dimensional repeating structures, see U.S. Pat. No. 7,428,060, entitled OPTIMIZATION OF DIFFRACTION ORDER SELECTION FOR TWO-DIMENSIONAL STRUCTURES, filed on Mar. 24, 2006, which is incorporated herein by reference in its entirety.

Figure 2:
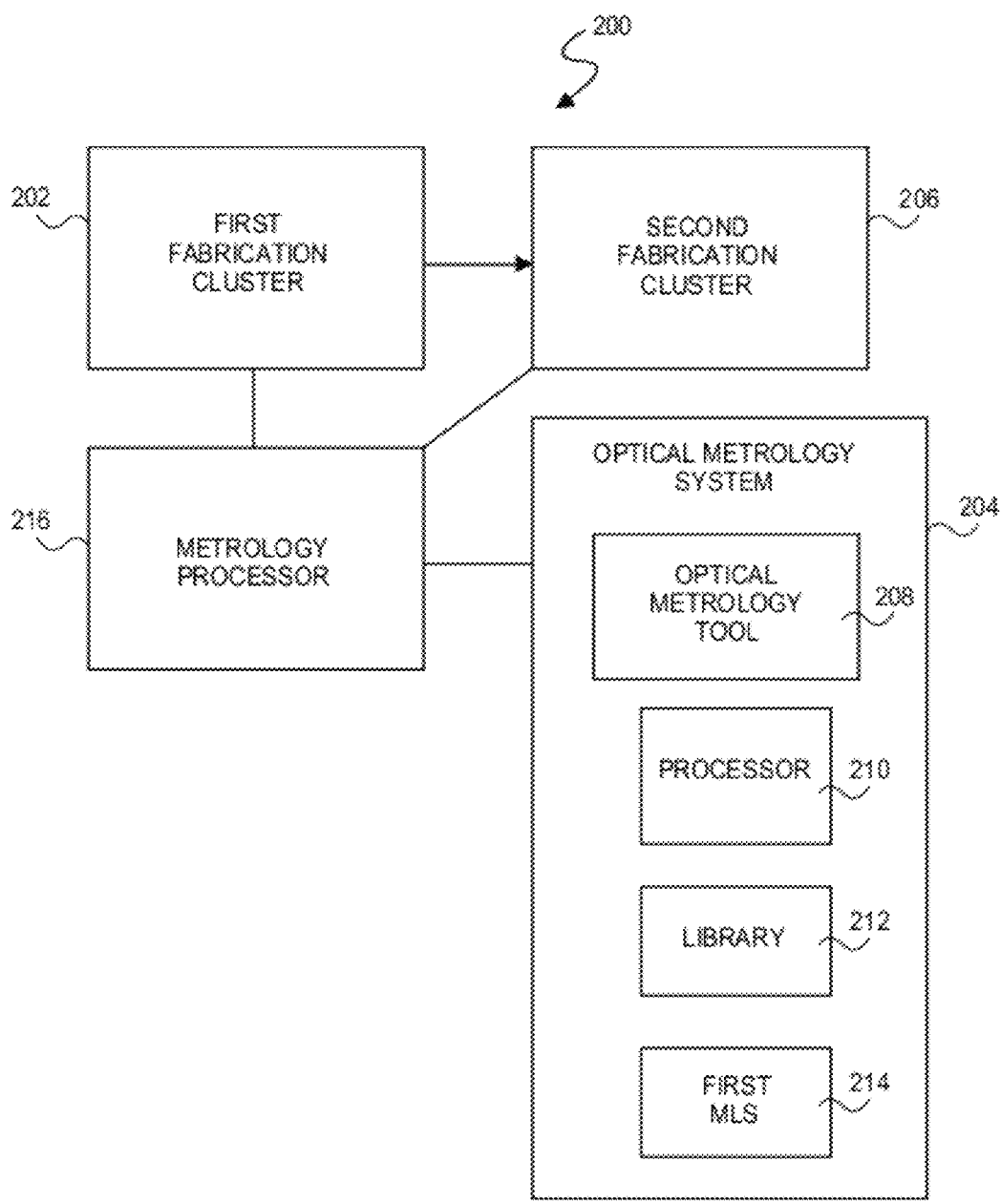
FIG. 2 is an exemplary block diagram of a system for determining and utilizing structural parameters for automated process and equipment control, in accordance with an embodiment of the present invention.

FIG. 2 is an exemplary block diagram of a system 200 for determining and utilizing structural parameters, such as profile or film thickness parameters, for automated process and equipment control, in accordance with an embodiment of the present invention. System 200 includes a first fabrication cluster 202 and optical metrology system 204. System 200 also includes a second fabrication cluster 206. Although the second fabrication cluster 206 is depicted in FIG. 2 as being subsequent to first fabrication cluster 202, it should be recognized that second fabrication cluster 206 can be located prior to first fabrication cluster 202 in system 200 (and, e.g., in the manufacturing process flow).

A photolithographic process, such as exposing and developing a photo-resist layer applied to a wafer, can be performed using first fabrication cluster 202. In one exemplary embodiment, optical metrology system 204 includes an optical metrology tool 208 and processor 210. Optical metrology tool 208 is configured to measure a diffraction signal obtained from the structure. If the measured diffraction signal and the simulated diffraction signal match, one or more values of the profile or film thickness parameters are determined to be the one or more values of the profile or film thickness parameters associated with the simulated diffraction signal.

In one exemplary embodiment, optical metrology system 204 can also include a library 212 with a plurality of simulated diffraction signals and a plurality of values of one or more profile or film thickness parameters associated with the plurality of simulated diffraction signals. As described above, the library can be generated in advance. Metrology processor 210 can compare a measured diffraction signal obtained from a structure to the plurality of simulated diffraction signals in the library. When a matching simulated diffraction signal is found, the one or more values of the profile or film thickness parameters associated with the matching simulated diffraction signal in the library is assumed to be the one or more values of the profile or film thickness parameters used in the wafer application to fabricate the structure.

System 200 also includes a metrology processor 216. In one exemplary embodiment, processor 210 can transmit the one or more values of the one or more profile or film thickness parameters to metrology processor 216. Metrology processor 216 can then adjust one or more process parameters or equipment settings of first fabrication cluster 202 based on the one or more values of the one or more profile or film thickness parameters determined using optical metrology system 204. Metrology processor 216 can also adjust one or more process parameters or equipment settings of the second fabrication cluster 206 based on the one or more values of the one or more profile or film thickness parameters determined using optical metrology system 204. As noted above, fabrication cluster 206 can process the wafer before or after fabrication cluster 202. In another exemplary embodiment, processor 210 is configured to train machine learning system 214 using the set of measured diffraction signals as inputs to machine learning system 214 and profile or film thickness parameters as the expected outputs of machine learning system 214.

In accordance with embodiments of the present invention, near field intensity contours for two or more wavelengths are compared for a given structural model. In the case of three-dimensional structures, in some embodiments, an appropriate azimuth angle is first determined prior to determining the near field intensity contours. In either case, from the comparison of contours, a structural model for OCD measurement comparison may then be improved or optimized.

In comparison to conventional approaches, embodiments of the present invention may be employed to significantly reduce the time needed to provide good model results. By comparison, in a conventional approach, there may be a number of contributing factors to the long time to optimize an OCD model. One major factor is the time needed to "guess" a correct shape model or filmstack thickness upon failure of a nominal model to provide a good chi-squared or good profile results. One or more embodiments described herein allow reduction in model optimization time by reducing the number of candidate model loops otherwise needed in conventional approaches.

Figure 3:
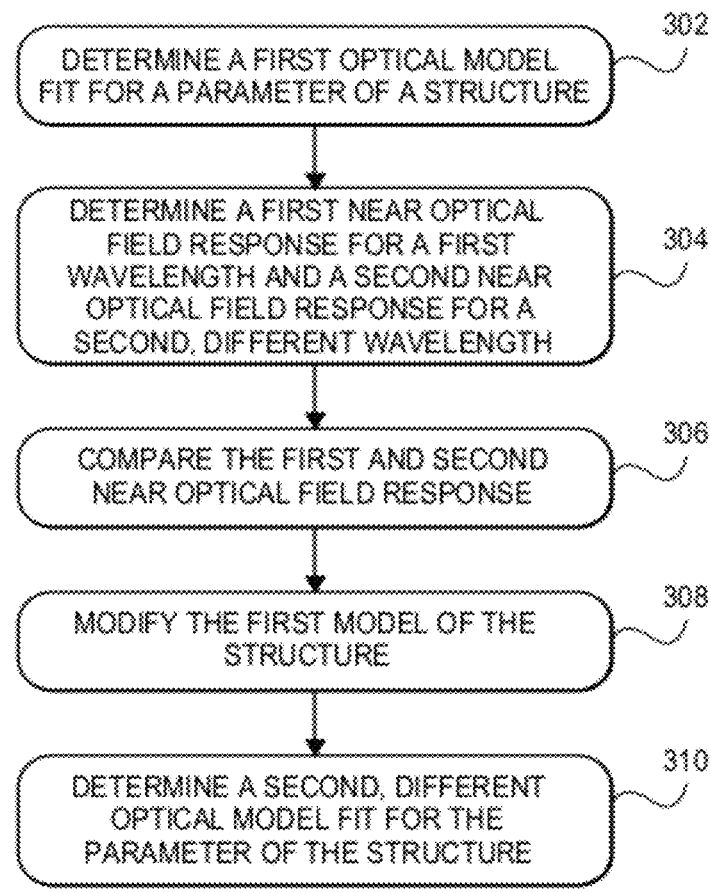
FIG. 3 depicts a flowchart representing operations in a method of optimizing optical parametric models for structural analysis using OCD metrology, in accordance with an embodiment of the present invention.

In an aspect of the present invention, a strategic approach to optimizing an optical model for two-dimensional or three-dimensional structures is provided. For example, FIG. 3 depicts a flowchart 300 representing operations in a method of optimizing optical parametric models for structural analysis using OCD metrology, in accordance with an embodiment of the present invention.

Referring to operation 302 of flowchart 300, a method of optimizing optical parametric models for structural analysis using OCD metrology includes determining a first optical model fit for a parameter of a structure. The first optical model fit is based on a domain of wavelengths for a first model of the structure.

In a poor or non-optimized optical model fit, often one or more portions of a spectrum show poor correlation between experimental data and model data. As an example, FIG. 4 includes plots 400 and 404 correlating measured structural data with model structural data versus a domain of wavelengths, in accordance with an embodiment of the present invention.

Figure 4:
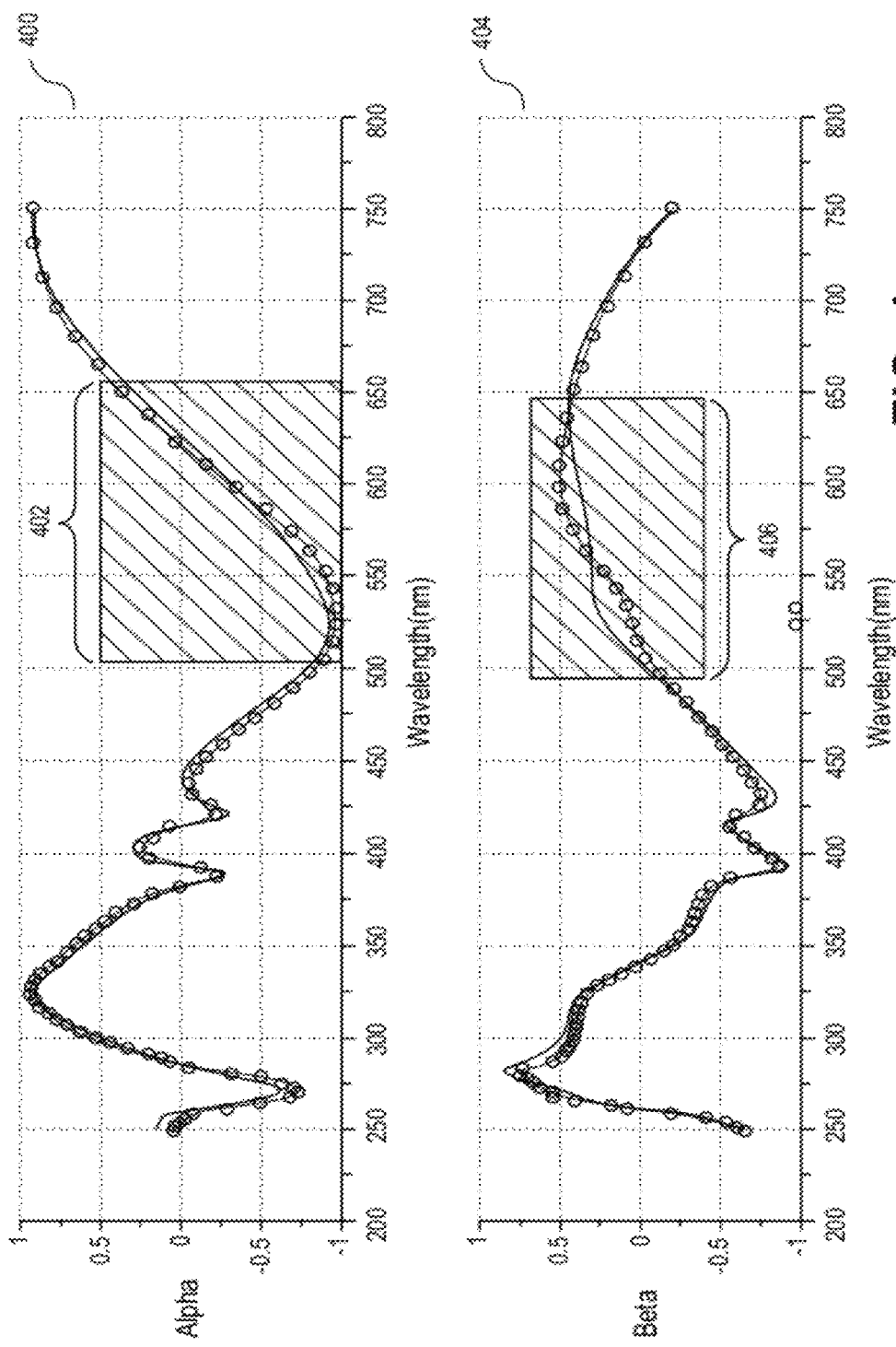
FIG. 4 includes plots correlating measured structural data with model structural data versus a domain of wavelengths, in accordance with an embodiment of the present invention.

Referring to FIG. 4, model data is represented by dots while experimental data is represented by lines. Region 402 of plot 400 and region 406 of plot 400 represent regions of poor correlation between model and experimental data. For example, on a bad lot, chi-squared can be as high as 1600 for some sites versus a typically good chi-squared of about 200. Regions 402 and 406 indicate that the fit quality is visibly poor in the wavelength range of 500-650 nanometers. The remainder of the method of flowchart 300 addresses option of how to change the model used to improve the fit between experimental and model data. In an embodiment, determining the first optical model fit for the parameter of the structure includes determining the first optical model fit for a shape of the structure or for a film thickness within the structure.

Figure 5:
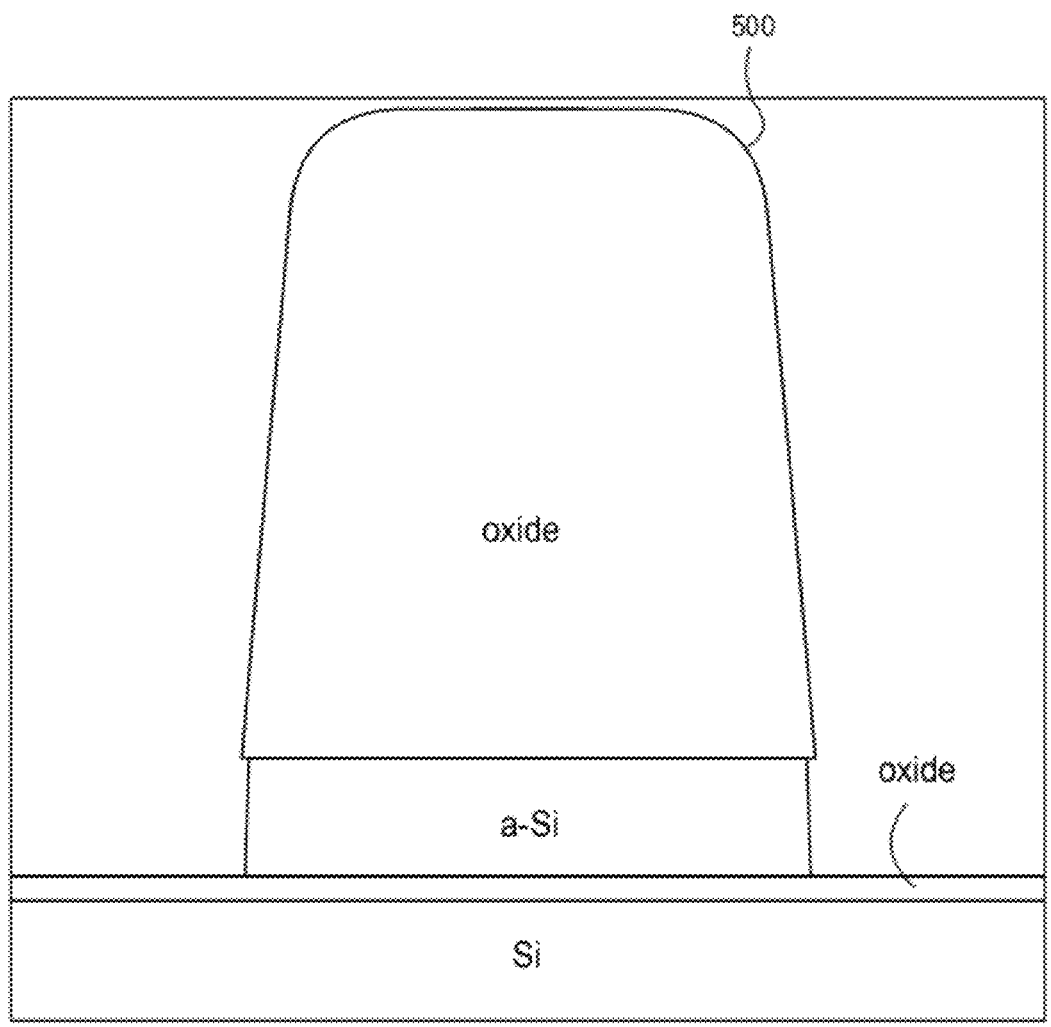
FIG. 5 illustrates a structural representation for modeling, in accordance with an embodiment of the present invention.

As an example of a model structure, FIG. 5 illustrates a structural representation 500 for modeling, in accordance with an embodiment of the present invention. In a conventional model improvement approach, even a structure as simple as 500 is associated with eight parameters and four shape regions. Any fixed parameters are test floated in the model. The shape of structure 500 is then modified (e.g., once per region) and additional parameters are floated, such as but not limited to, a refractive index parameter. The correlation is rechecked for averaging and slabbing issues. By contrast to such a trial and error approach, operations 304-310 below describe a more rigorous and concerted approach to improving model data fitting.

Referring to operation 304 of flowchart 300, the method of optimizing optical parametric models for structural analysis using OCD metrology also includes determining a first near optical field response for a first wavelength of the domain of wavelengths and a second near optical field response for a second, different wavelength of the domain of wavelengths.

In an embodiment, determining the first and second near optical field responses includes selecting the first and second wavelengths from a region of low correlation of the first optical model fit, such as from regions 402 and 406 of plots 400 and 404, respectively. In one such embodiment, selecting the first and second wavelengths from a region of low correlation of the first optical model fit includes selecting an angle of incidence for the first wavelength and using the angle of incidence for the second wavelength. As an example, at a given wavelength, near field optical intensities may be measured or calculated at two or more different angles of incidence (AOI), such as at 0 and 70 degrees AOI. It is to be understood throughout that more than two wavelengths may be used and compared.

In an embodiment, determining the first and second near optical field responses includes generating a pair of contour plots. In an embodiment, the first and second near optical field responses are based on the polarization state of the incident light such as S-polarized light, P-polarized light, or both, as exemplified below.

Referring to operation 306 of flowchart 300, the method of optimizing optical parametric models for structural analysis using OCD metrology also includes comparing the first and second near optical field responses to locate a common region of high optical field intensity for the parameter of the structure.

The optical field intensity may be displayed as a function of position as, e.g., a color contour plot overlaid on a drawing of the device or filmstack cross section. The contour plot may be displayed for different polarization states (e.g., S, or P, or both), and optical wavelengths, of the incident light illumination. The polarization states considered need not be limited to S and P polarization. Any linear, circular or elliptical polarization state of the incident light or unpolarized incident light may be considered. The plots may also show the near optical fields corresponding to any individual element of the Jones matrix or Mueller matrix of the reflectivity of the structure, or any combination of elements of the Jones matrix or Mueller matrix. In an embodiment, as described above, a field distribution is calculated at wavelengths for which the optical model fit quality is poor. Regions of the device or filmstack at which the optical field strength is large may then be identified. In an embodiment, the first and second near optical field responses are compared, and the comparing includes comparing the pair of contour plots described in association with operation 304 and exemplified in FIGS. 6, 7 and 8, described below. As an example, a determination of commonality of regions of high field intensity for plots within a given wavelength (e.g., 200 nanometers) and at a new wavelength (e.g., 600 nanometers) is made. This determination of commonality may be performed following, prior to, or in conjunction with, a selection of AOI at the given wavelength.

In cases where the optical near field strength is low, then even if critical dimension shape of film thickness varies, the effect on the far field (the detected field) is low. However, in cases where the optical near field is stronger, the effect of profile changes is stronger. This comparison does not guarantee uniqueness. However, in one embodiment, such a situation having certain limited portions of the wavelength range that fit poorly typically do correlate with the regions of the model that require the most significant alteration.

Upon comparison of the contour plots at different wavelengths, the local optical field strength for the wavelengths within a problem zone may be computed. Shape modification efforts may then be targeted in or near the region of the problem zone. That is, if optical wavelengths have fields known to tend to be high, then the regions of the high fields are likely candidates for targeting model alteration. In one embodiment, a comparison at different wavelengths increases certainty of appropriate region alteration if high intensity fields are generated in the same region(s) at both wavelengths.

Figure 6:
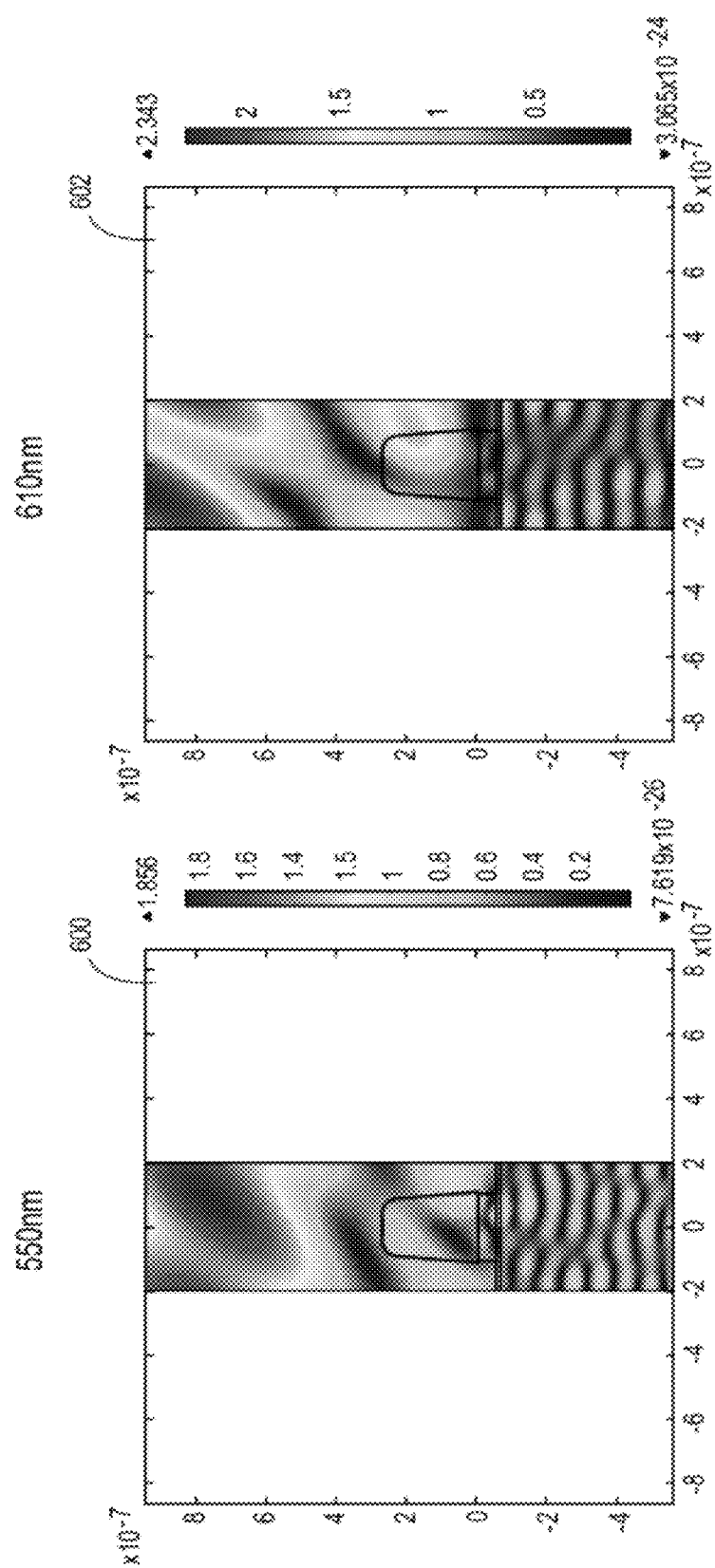
FIG. 6 includes contour plots of near field intensities at wavelengths of 550 nanometers and 610 nanometers, respectively, for an S-polarized field incident on a test structure, in accordance with an embodiment of the present invention.

As an example, FIG. 6 includes contour plots 600 and 602 of near field intensities at wavelengths of 550 nanometers and 610 nanometers, respectively, for an S-polarized field of a test structure, in accordance with an embodiment of the present invention. In this example, there exists no obvious region in common between the two wavelengths.

Figure 7:
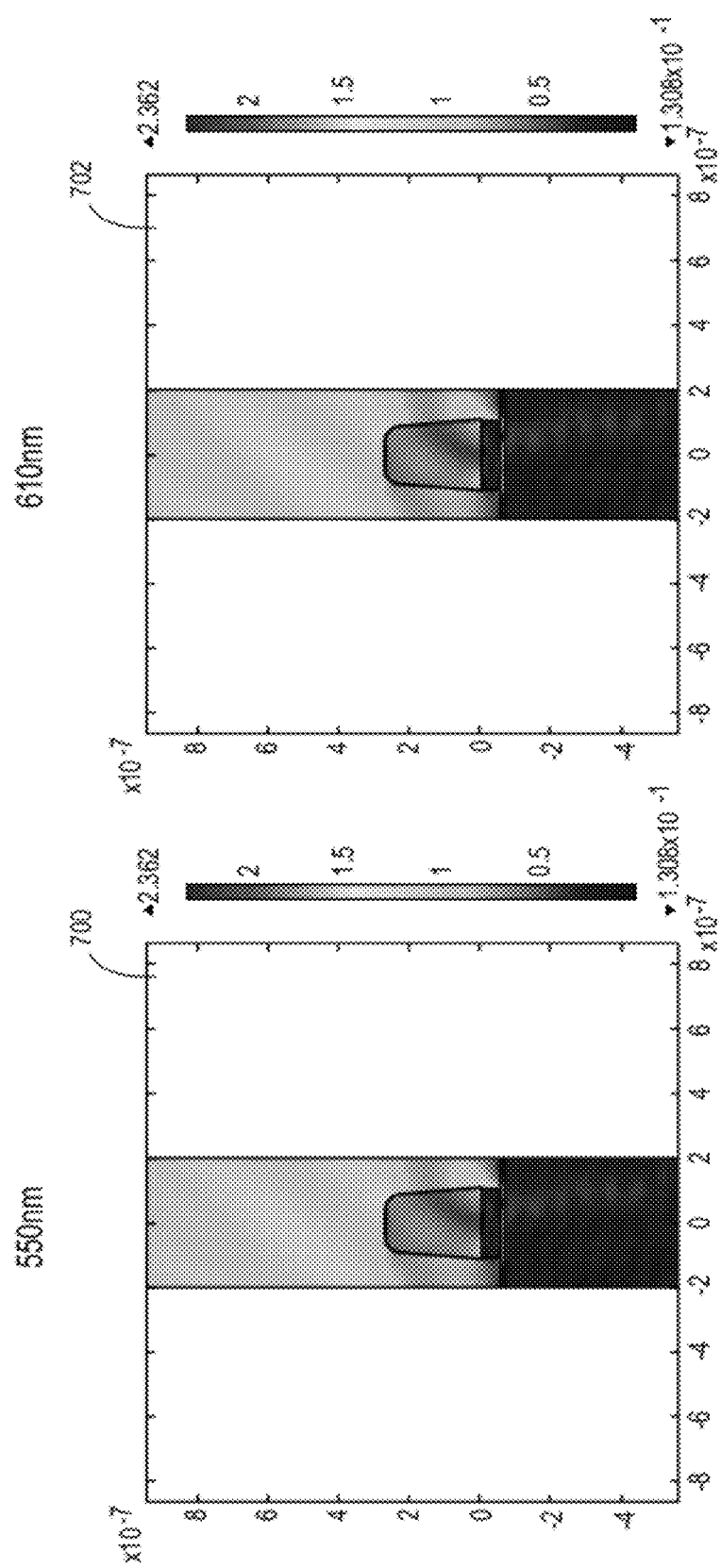
FIG. 7 includes contour plots of near field intensities at wavelengths of 550 nanometers and 610 nanometers, respectively, for a P-polarized field incident on a test structure, in accordance with an embodiment of the present invention.
Figure 8:
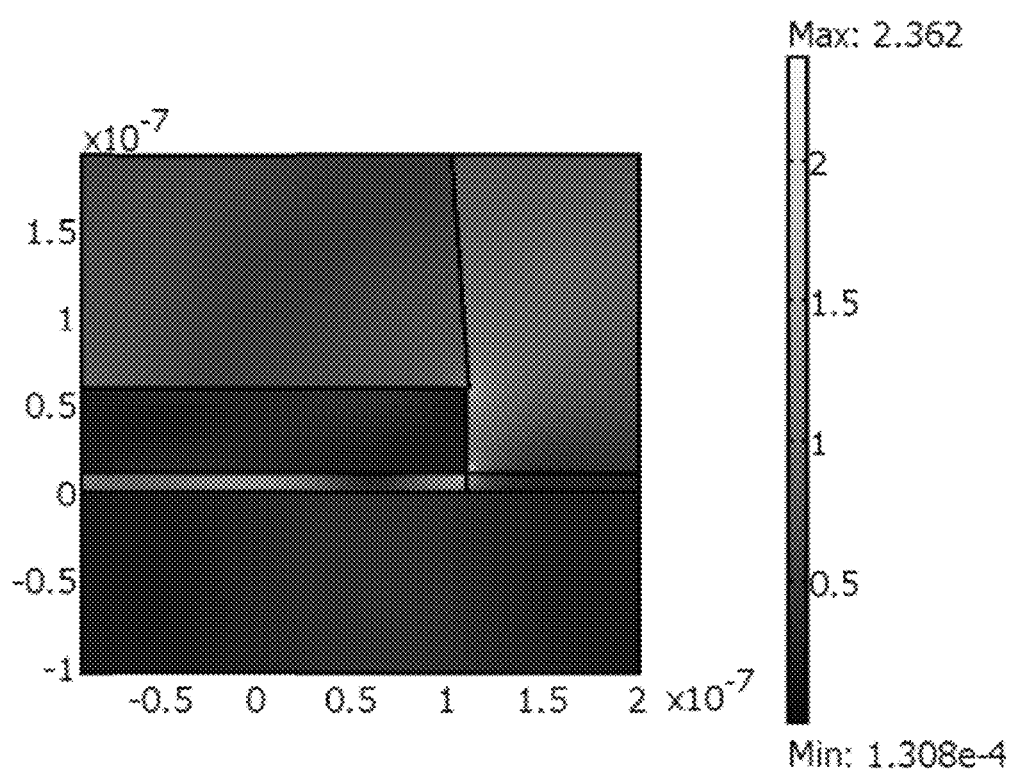
FIG. 8 is a magnified contour plot of near field intensities at for a P-polarized field incident on the test structure of FIG. 7, in accordance with an embodiment of the present invention.

As a contrasting example, FIG. 7 includes contour plots 700 and 702 of near field intensities at wavelengths of 550 nanometers and 610 nanometers, respectively, for a P-polarized field incident on a test structure, in accordance with an embodiment of the present invention. FIG. 8 is a magnified contour plot 800 of near field intensities at a wavelength of 610 nanometers for a P-polarized field incident on the test structure of FIG. 7. In this example, a bottom oxide and lower right corner of the structure have high fields.

Figure 9:
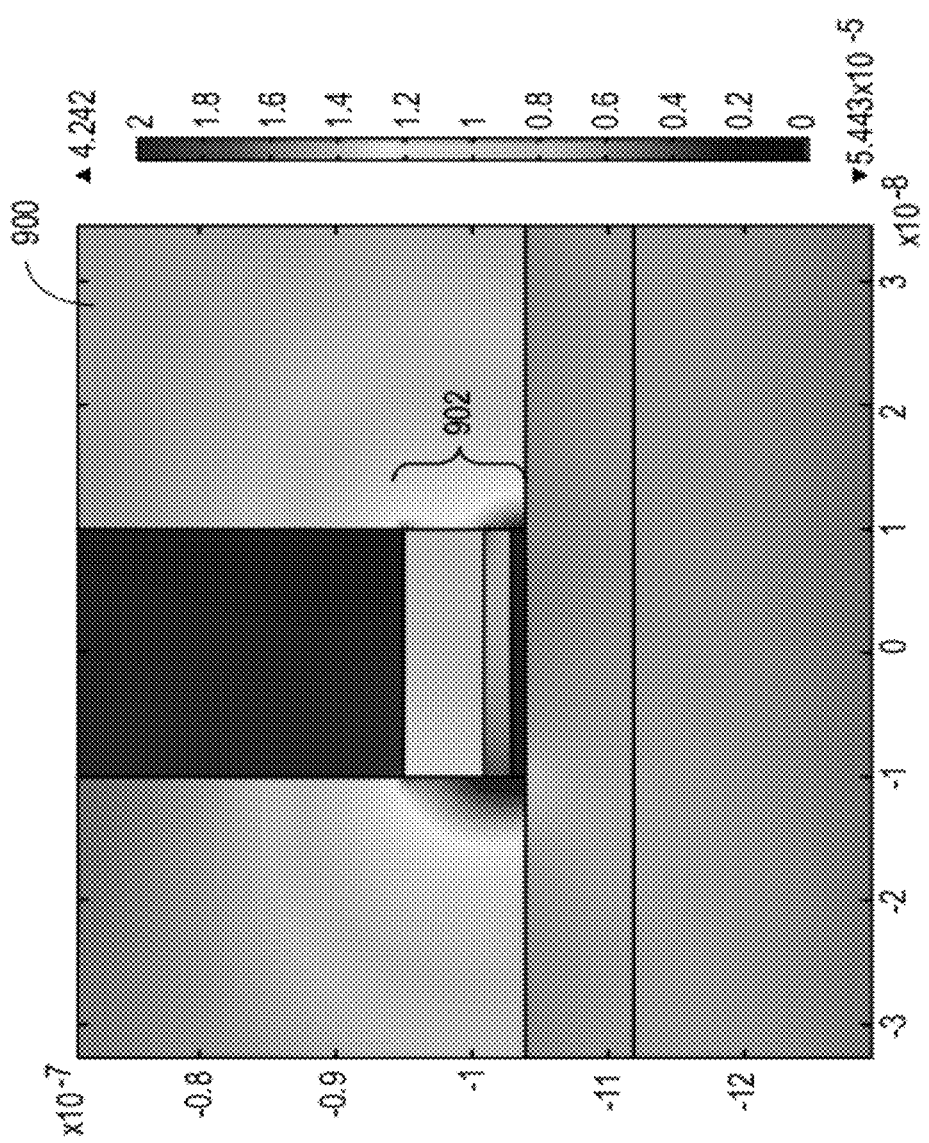
FIG. 9 is a contour plot of near field intensities for a P-polarized field incident on a test structure including high-k and metal gate layers, in accordance with an embodiment of the present invention.

FIGS. 6, 7 and 8 illustrate a structural shape with a region of high intensity. As an example of film thickness parameters requiring alteration in a model structure, FIG. 9 is a contour plot 900 of near field intensities for a P-polarized field of a test structure including high-k and metal gate layers, in accordance with an embodiment of the present invention. Referring to FIG. 9, optical field strength is high near high-k and metal gate layers, indicated as region 902. In such an embodiment, an altered model may include a changed thickness for one or both of the high-k and metal gate layers.

Referring to operation 308 of flowchart 300, the method of optimizing optical parametric models for structural analysis using OCD metrology also includes modifying the first model of the structure to provide a second, different model of the structure.

In an embodiment, the regions of high near field optical intensity are the very regions which will affect the model fit quality the greatest. By contrast, regions with little or no optical field have little ability to alter the diffracted/reflected far field intensity, even if the device shape or filmstack thickness changes. Accordingly, in one embodiment, a model structure is changed or altered in the region where the near optical field strength is large, and the new candidate model structure is tested. A targeted determination is then made as to how to optimize the model, based at least in part on the information in the optical field strength plot(s). Then, referring to operation 310 of flowchart 300, the method of optimizing optical parametric models for structural analysis using OCD metrology also includes determining a second, different optical model fit for the parameter of the structure based on the second model of the structure.

Figure 10:
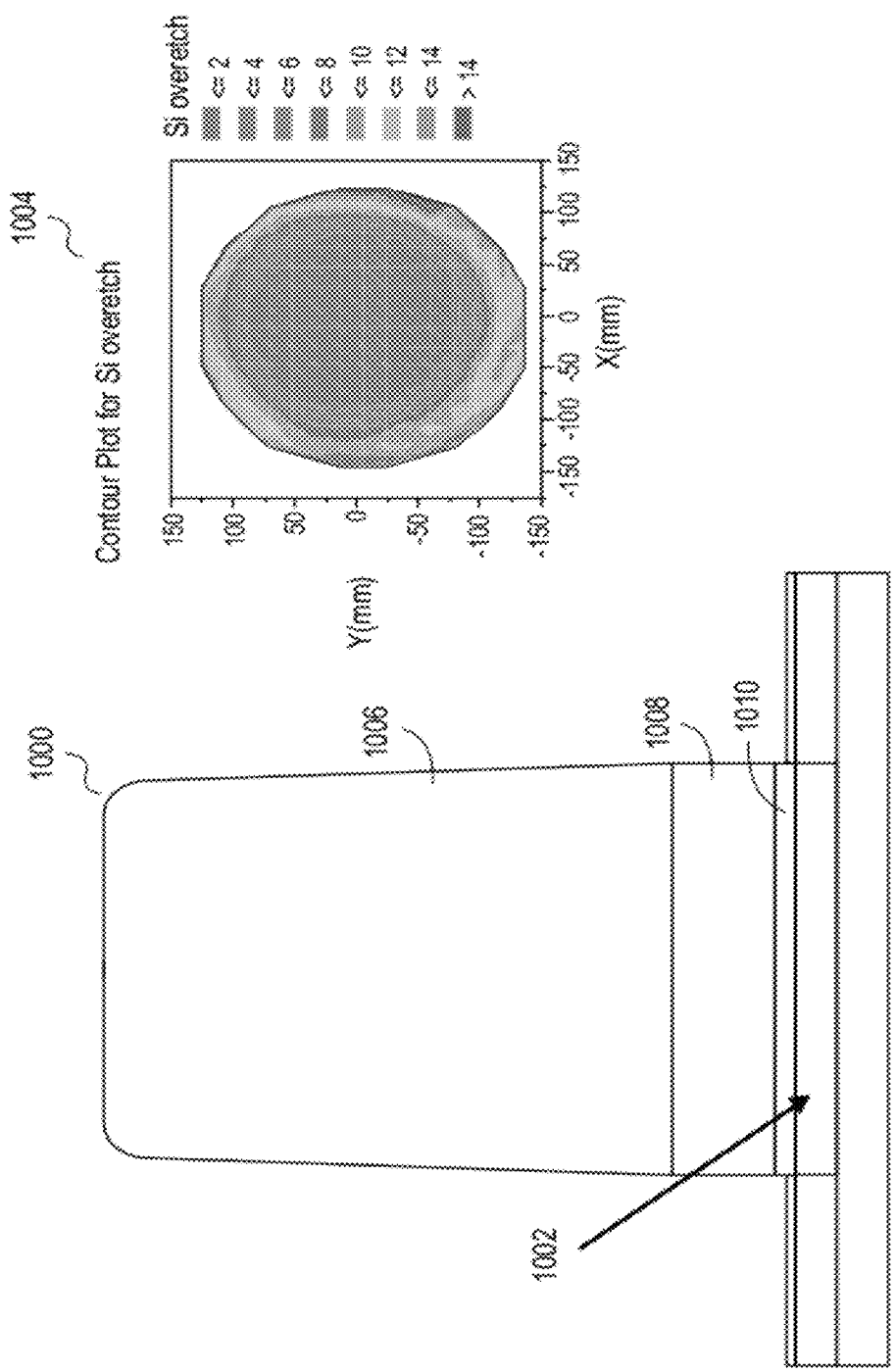
FIG. 10 illustrates a modified structural representation for modeling, in accordance with an embodiment of the present invention.

As an example, FIG. 10 illustrates a modified structural representation 1000 for modeling, in accordance with an embodiment of the present invention. As compared with the starting model structure 500 of FIG. 5, the new model 1000 adds a silicon over-etch trapezoid 1002 in the substrate. In contrast to a broad trial and error approach, however, oxide layer 1006, a-Si (amorphous silicon) layer 1008 and thin oxide layer 1010 are left unchanged. The determination to add only a silicon over-etch trapezoid 1002 in the substrate based on near field intensities, as described above, is consistent with contour plot 1004. In contour plot 1004, it is revealed that the height of the silicon over-etch trapezoid is larger at the wafer edge, i.e., an issue of etch non-uniformity is exposed. Thus, in this example, a better suited model structure was obtained by only adding one parameter (the height of the new silicon over-etch trapezoid 1002) without the time-consuming approach of first floating all fixed parameters in structure 500, which would not have arrived at as good a model of the structure as 1000 since the structure 500 did not contain the over-etch trapezoid 1002.

As demonstrated in the embodiments associated with flowchart 300, optical field plots are useful for diagnosing applications model fitting problems. For example, targeted efforts may be used to improve the shape model to reveal measurement physics, rendering applications model optimization decisions more rigorous and less "trial and error." Furthermore, selection of correct or appropriate wavelengths may provide enhanced sensitivity for critical parameters in certain layers, e.g., film thickness parameters.

It is to be understood that more than one iteration of the combination of operations 302-310 of flowchart 300 may be used to arrive at a desired model fit. Thus, in accordance with an embodiment of the present invention, the method of optimizing optical parametric models for structural analysis using OCD metrology further includes determining a third, different optical model fit for the parameter of the structure based on a third model of the structure.

Figure 11A:
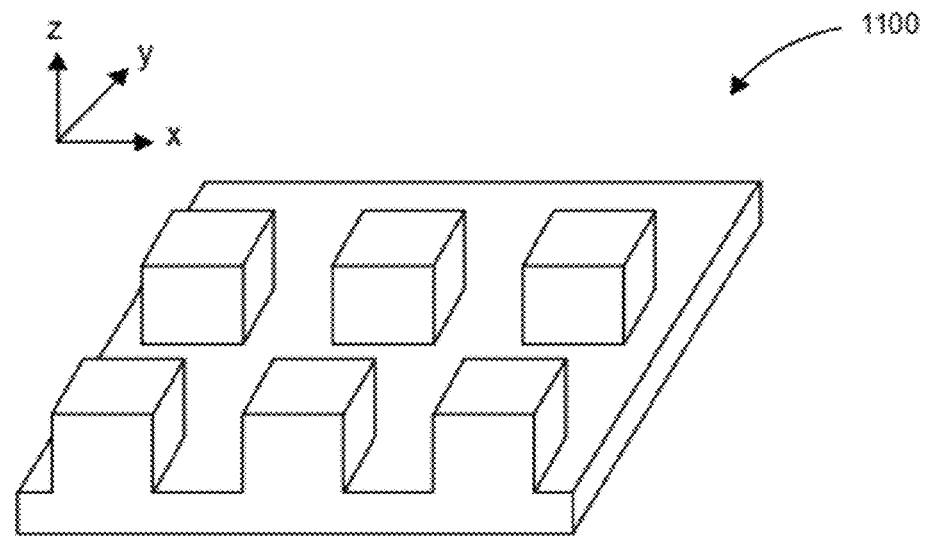
FIG. 11A depicts a periodic grating having a profile that varies in the x-y plane, in accordance with an embodiment of the present invention.

In an embodiment, optimizing the optical model includes using a three-dimensional grating structure. The term "three-dimensional grating structure" is used herein to refer to a structure having an x-y profile that varies in two horizontal dimensions in addition to a depth in the z-direction. For example, FIG. 11A depicts a periodic grating 1100 having a profile that varies in the x-y plane, in accordance with an embodiment of the present invention. The profile of the periodic grating varies in the z-direction as a function of the x-y profile.

Figure 11B:
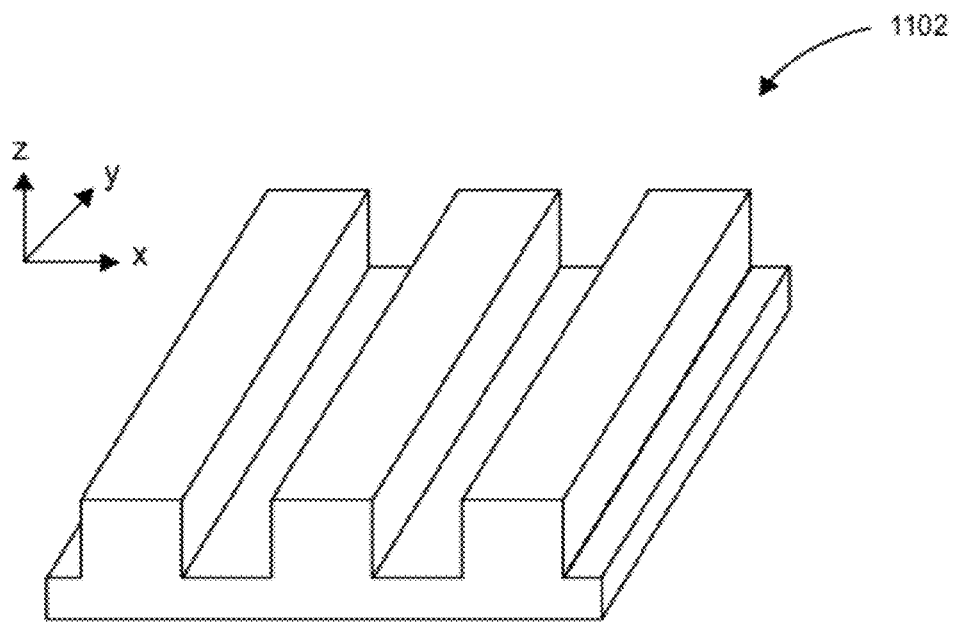
FIG. 11B depicts a periodic grating having a profile that varies in the x-direction but not in the y-direction, in accordance with an embodiment of the present invention.

In an embodiment, optimizing the optical model includes using a two-dimensional grating structure. The term "two-dimensional grating structure" is used herein to refer to a structure having an x-y profile that varies in only one horizontal dimension in addition to a depth in the z-direction. For example, FIG. 11B depicts a periodic grating 1102 having a profile that varies in the x-direction but not in the y-direction, in accordance with an embodiment of the present invention. The profile of the periodic grating varies in the z-direction as a function of the x profile. It is to be understood that the lack of variation in the y-direction for a two-dimensional structure need not be infinite, but any breaks in the pattern are considered long range, e.g., any breaks in the pattern in the y-direction are spaced substantially further apart than the breaks in the pattern in the x-direction.

Figure 12:
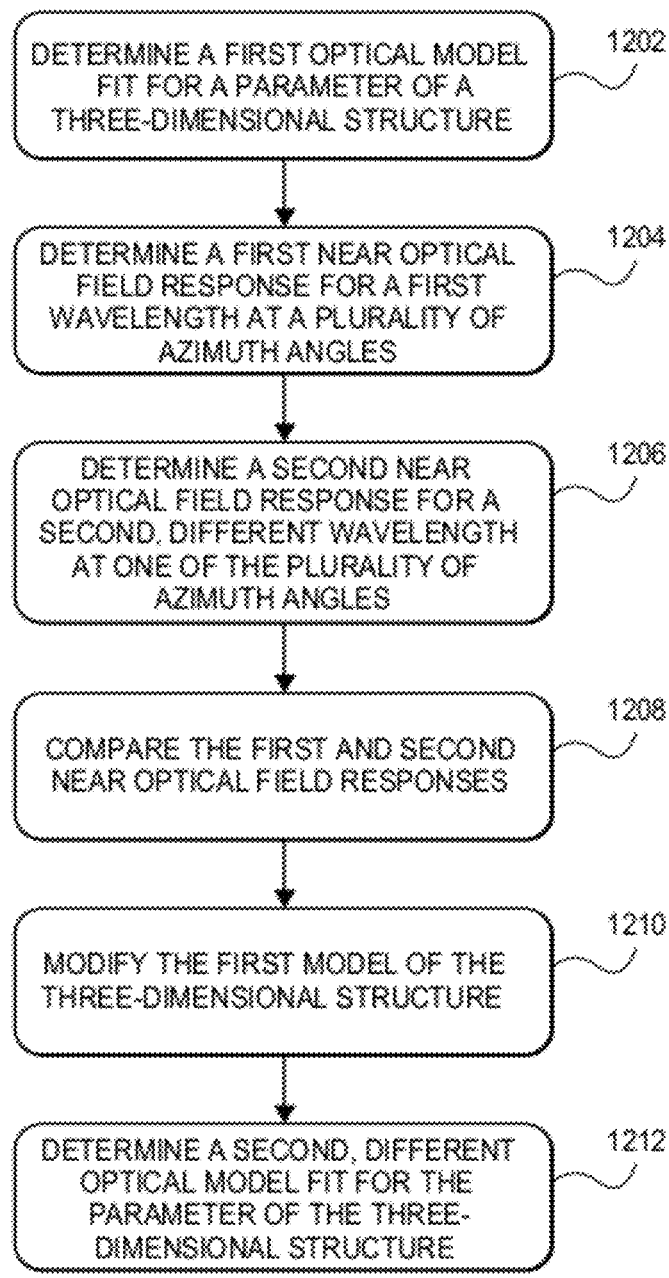
FIG. 12 depicts a flowchart representing operations in a method of optimizing optical parametric models for three-dimensional structural analysis using OCD metrology, in accordance with an embodiment of the present invention.

Further to the above described methodology, an appropriate azimuth angle for investigation may first be determined, prior to comparing contour plots for local regions of high field intensity. In an aspect of the present invention, a strategic approach to optimizing an optical model for two-dimensional or three-dimensional structures is provided. For example, FIG. 12 depicts a flowchart 1200 representing operations in a method of optimizing optical parametric models for three-dimensional structural analysis using OCD metrology, in accordance with an embodiment of the present invention.

Figure 13:
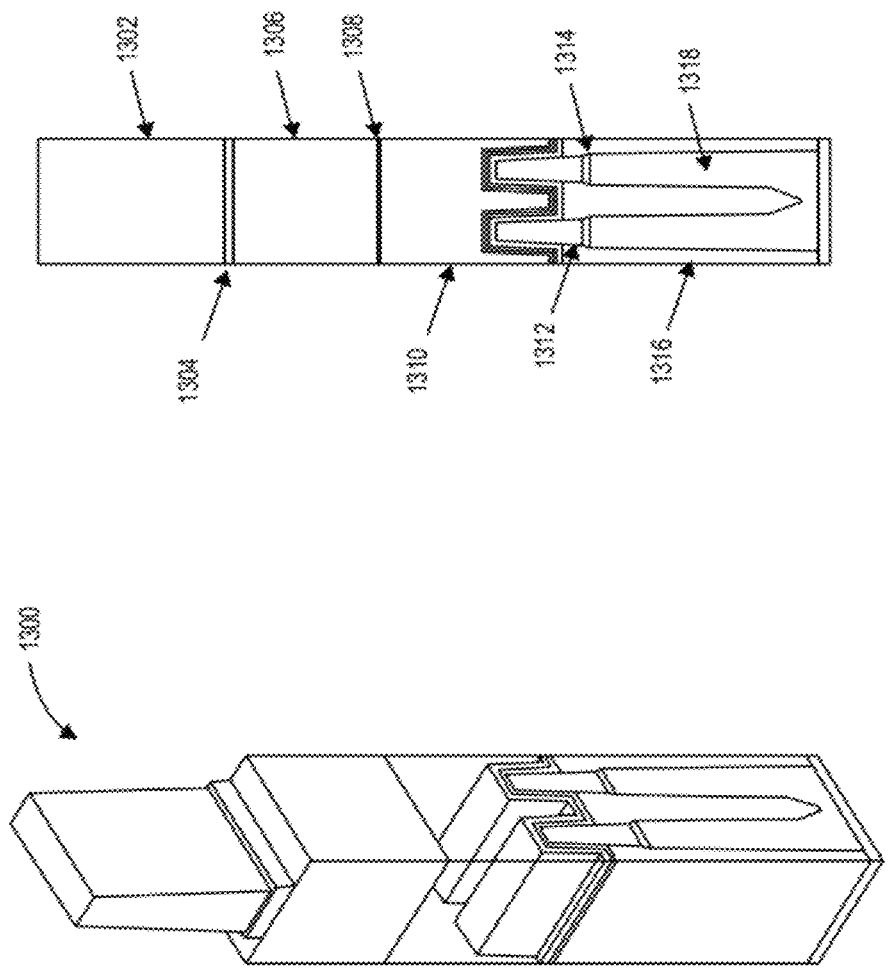
FIG. 13 illustrates a three-dimensional test structure, in accordance with an embodiment of the present invention.

A three-dimensional test structure may be provided. As an example, FIG. 13 illustrates a three-dimensional test structure 1300, in accordance with an embodiment of the present invention. In one such embodiment, structure 1300 is a device for three-dimensional flash memory. The structure may include, but is not limited to or limited by, an oxide etch mask 1302, a nitride overetch layer 1304, a nitride layer 1306, an interface oxide-nitride-oxide (ONO) blocking dielectric 1308, a polysilicon control gate 1310, a polysilicon floating gate 1312 which may be isolated from the polysilicon control gate 1310 by a dielectric layer or stack of dielectric layers, an oxide tunnel dielectric 1314, an oxide fill layer 1316, and crystalline silicon 1318.

Referring to operation 1202 of flowchart 1200, a method of optimizing optical parametric models for three-dimensional structural analysis using OCD metrology includes determining a first optical model fit for a parameter of a three-dimensional structure. The first optical model fit is based on a domain of wavelengths for a first model of the three-dimensional structure. An example may be similar to the example of FIG. 4 associated with operation 302 of flowchart 300. In one embodiment, determining the first optical model fit for the parameter of the three-dimensional structure includes determining the first optical model fit for a shape of the three-dimensional structure or for a film thickness within the three-dimensional structure.

Figure 14:
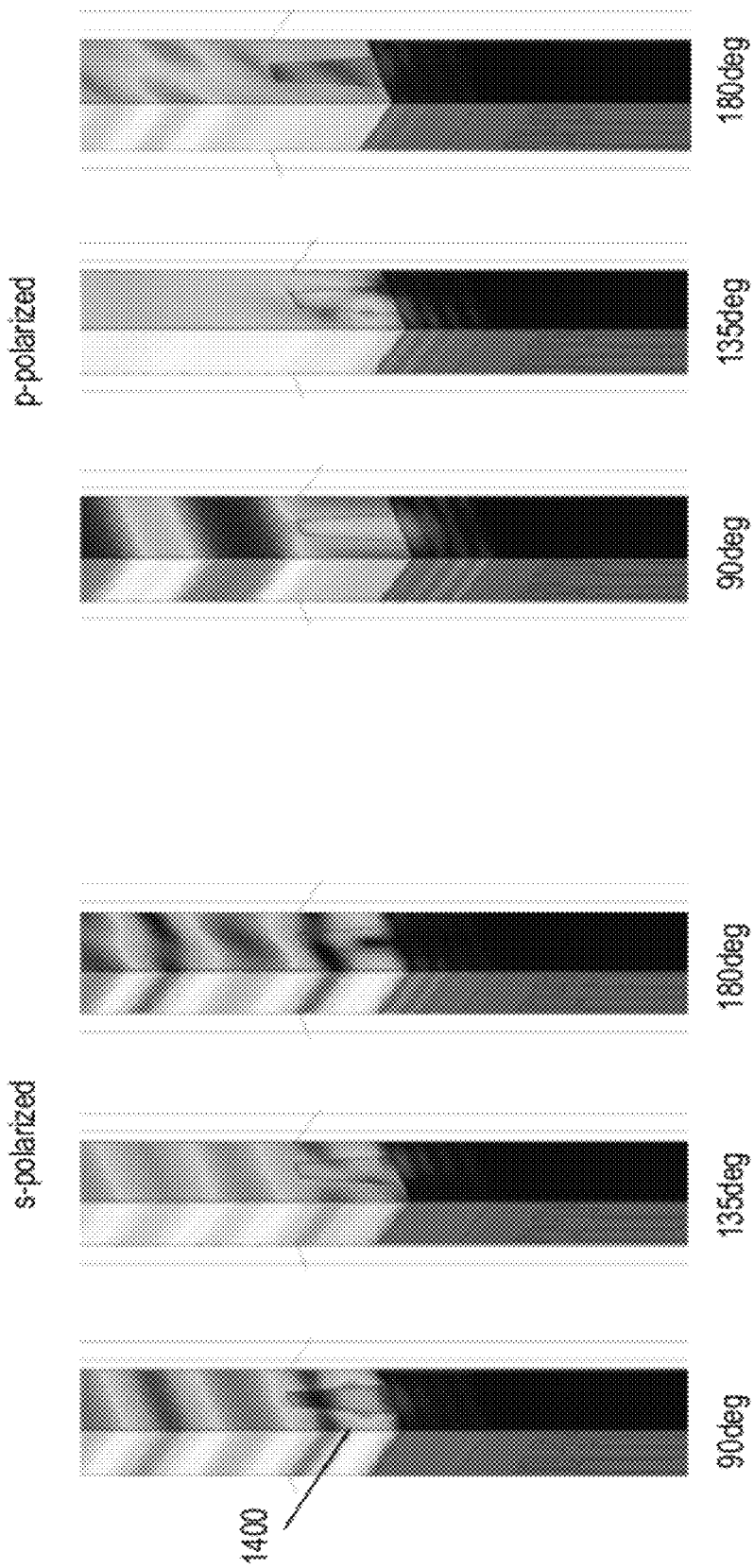
FIG. 14 includes contour plots of near field intensities at 200 nanometers for S- and P-polarized incident fields, at azimuth angles of 90 degrees, 135 degrees and 180 degrees, for the test structure of FIG. 13, in accordance with an embodiment of the present invention.

Referring to operation 1204, the method also includes determining a first near optical field response for a first wavelength of the domain of wavelengths at a plurality of azimuth angles. As an example, FIG. 14 includes contour plots of near field intensities at 200 nanometers for S- and P-polarized fields, at azimuth angles of 90 degrees, 135 degrees and 180 degrees, for the test structure of FIG. 13, in accordance with an embodiment of the present invention. Referring to FIG. 14, a field enhancement region 1400 is located for S-polarized near field light at an azimuth angle of 90 degrees.

Referring to operation 1206, the method also includes determining a second near optical field response for a second, different wavelength of the domain of wavelengths at one of the plurality of azimuth angles. For example, S-polarized light at a wavelength other than 200 nanometers at an azimuth angle of 90 degrees may be used to generate a comparison plot for the structure of FIG. 14. In one such embodiment, determining the first and second near optical field responses includes selecting the first and second wavelengths from a region of low correlation of the first optical model fit. In a specific such embodiment, selecting the first and second wavelengths from a region of low correlation of the first optical model fit includes selecting an angle of incidence for the first wavelength and using the angle of incidence for the second wavelength.

Referring to operation 1208, the method also includes comparing the first and second near optical field responses to locate a common region of high optical field intensity for the parameter of the three-dimensional structure. In one embodiment, determining the first and second near optical field responses includes generating a pair of contour plots, and comparing the first and second near optical field responses includes comparing the pair of contour plots. Then, in operation 1210, the first model of the three-dimensional structure is modified to provide a second, different model of the three-dimensional structure.

Referring to operation 1212, the method finally includes determining a second, different optical model fit for the parameter of the three-dimensional structure based on the second model of the three-dimensional structure. However, in one embodiment, the method further includes determining a third, different optical model fit for the parameter of the three-dimensional structure based on a third model of the three-dimensional structure.

Embodiments of the present invention, such as the methods described in association with flowcharts 300 and 1200, may be applied in a variety of contexts, with a variety of possible benefits from their employment. For example, in an embodiment, one or more of the approaches described herein may be used for optimizing OCD shape models using the near optical field distribution. In an embodiment, a method of optimizing film thickness models using the near optical field distribution is provided. In an embodiment, methods herein include the use of the near optical field distribution at different polarizations to optimize optical parametric models. In an embodiment, the near optical field is employed to rank shape regions of the OCD model for alteration. In an embodiment, the near optical field is used to rank material regions of the OCD model for alteration.

In an embodiment, one or more of the approaches described herein may include the use of the near optical field to rank material regions or thicknesses of a film thickness model for alteration. In an embodiment, use of the near optical field distribution at several wavelengths to optimize an OCD or film thickness model is performed. In an embodiment, a method of identifying regions of the model with the largest near optical field, and subsequently performing model changes to improve model quality is provided. In an embodiment, information from the near optical field distribution at several wavelengths is used to identify common regions of large near optical field strength. In one such embodiment, a higher priority is assigned for optical model alteration and model improvement. In an embodiment, a method includes the use of correlation functions between optical field distributions at different wavelengths to semi-quantitatively identify regions of a device optical parametric model for alteration and optical model quality improvement.

The above methods may be implemented in an OCD product such as "Acushape" as a utility for an applications engineer to use after initial or preliminary models have been tested. Also, commercially available software such as "COMSOL Multiphysics" may be used to identify regions of an OCD model for alteration. The simulation results from such a software application may be used to predict a region for successful model improvement.

In an embodiment, the method of optimizing the optical model further includes altering parameters of a process tool based on an optimized parameter. A concerted altering of the process tool may be performed by using a technique such as, but not limited to, a feedback technique, a feed-forward technique, and an in situ control technique.

In accordance with an embodiment of the present invention, the method of optimizing the optical model further includes comparing a simulated spectrum to a sample spectrum. In one embodiment, a set of diffraction orders is simulated to represent diffraction signals from a two- or three-dimensional grating structure generated by an ellipsometric optical metrology system, such as the optical metrology system 1600 described below in association with FIG. 16A. However, it is to be understood that the same concepts and principles equally apply to the other optical metrology systems, such as reflectometric systems. The diffraction signals represented may account for features of the two- and three-dimensional grating structure such as, but not limited to, profile, dimension, material composition, or film thickness.

Embodiments of the present invention may be suitable for a variety of film stacks. For example, in an embodiment, a method for optimizing a parameter of a CD profile or structure is performed for a film stack including an insulating film, a semiconductor film and a metal film formed on a substrate. In an embodiment, the film stack includes a single layer or multiple layers. Also, in an embodiment invention, an analyzed or measured grating structure includes both a three-dimensional component and a two-dimensional component. For example, the efficiency of a computation based on simulated diffraction data may be optimized by taking advantage of the simpler contribution by the two-dimensional component to the overall structure and the diffraction data thereof.

Figure 15:
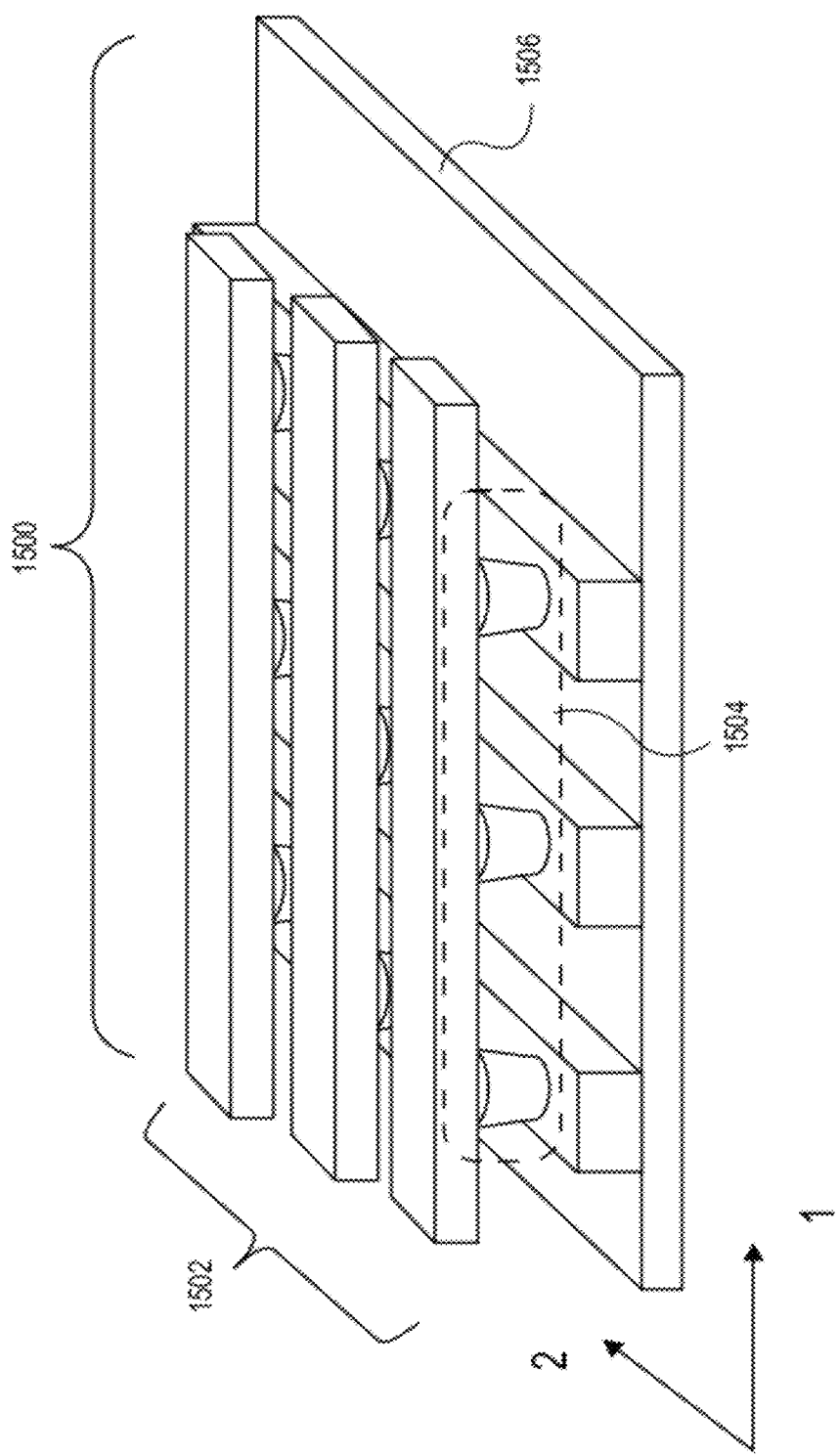
FIG. 15 represents a cross-sectional view of a structure having both a two-dimensional component and a three-dimensional component, in accordance with an embodiment of the present invention.

FIG. 15 represents a cross-sectional view of a structure having both a two-dimensional component and a three-dimensional component, in accordance with an embodiment of the present invention. Referring to FIG. 15, a structure 1500 has a two-dimensional component 1502 and a three-dimensional component 1504 above a substrate 1506. The grating of the two-dimensional component runs along direction 2, while the grating of the three-dimensional component runs along both directions 1 and 2. In one embodiment, direction 1 is orthogonal to direction 2, as depicted in FIG. 15. In another embodiment, direction 1 is non-orthogonal to direction 2.

Figure 16A:
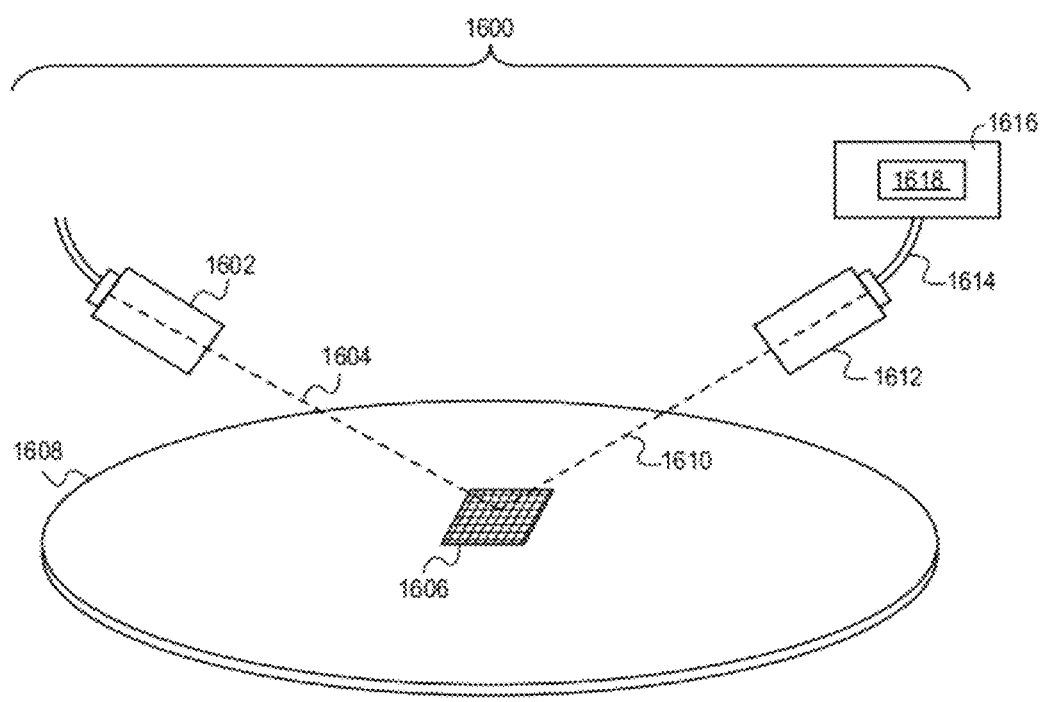
FIGS. 16A and 16B are two architectural diagrams illustrating the utilization of optical metrology to determine parameters of structures on a semiconductor wafer, in accordance with embodiments of the present invention.

FIG. 16A is an architectural diagram illustrating the utilization of optical metrology to determine parameters of structures on a semiconductor wafer, in accordance with embodiments of the present invention. The optical metrology system 1600 includes a metrology beam source 1602 projecting a metrology beam 1604 at the target structure 1606 of a wafer 1608. The metrology beam 1604 is projected at an incidence angle θ towards the target structure 1606 (θ is the angle between the incident beam 1604 and a normal to the target structure 1606). The ellipsometer may, in one embodiment, use an incidence angle of approximately 60° to 70°, or may use a lower angle (possibly close to 0° or near-normal incidence) or an angle greater than 70° (grazing incidence). The diffraction beam 1610 is measured by a metrology beam receiver 1612. The diffraction beam data 1614 is transmitted to a profile application server 1616. The profile application server 1616 may compare the measured diffraction beam data 1614 against a library 1618 of simulated diffraction beam data representing varying combinations of critical dimensions of the target structure and resolution.

In one exemplary embodiment, the library 1618 instance best matching the measured diffraction beam data 1614 is selected. It is to be understood that although a library of diffraction spectra or signals and associated hypothetical profiles is frequently used to illustrate concepts and principles, the present invention applies equally to a data space including simulated diffraction signals and associated sets of profile parameters, such as in regression, neural network, and similar methods used for profile extraction. The hypothetical profile and associated critical dimensions of the selected library 1616 instance is assumed to correspond to the actual cross-sectional profile and critical dimensions of the features of the target structure 1606. The optical metrology system 1600 may utilize a reflectometer, an ellipsometer, or other optical metrology device to measure the diffraction beam or signal.

In order to facilitate the description of embodiments of the present invention, an ellipsometric optical metrology system is used to illustrate the above concepts and principles. It is to be understood that the same concepts and principles apply equally to the other optical metrology systems, such as reflectometric systems. In an embodiment, the optical scatterometry is a technique such as, but not limited to, optical spectroscopic ellipsometry (SE), beam-profile reflectometry (BPR), beam-profile ellipsometry (BPE), and ultra-violet reflectometry (UVR). In a similar manner, a semiconductor wafer may be utilized to illustrate an application of the concept. Again, the methods and processes apply equally to other work pieces that have repeating structures.

Figure 16B:
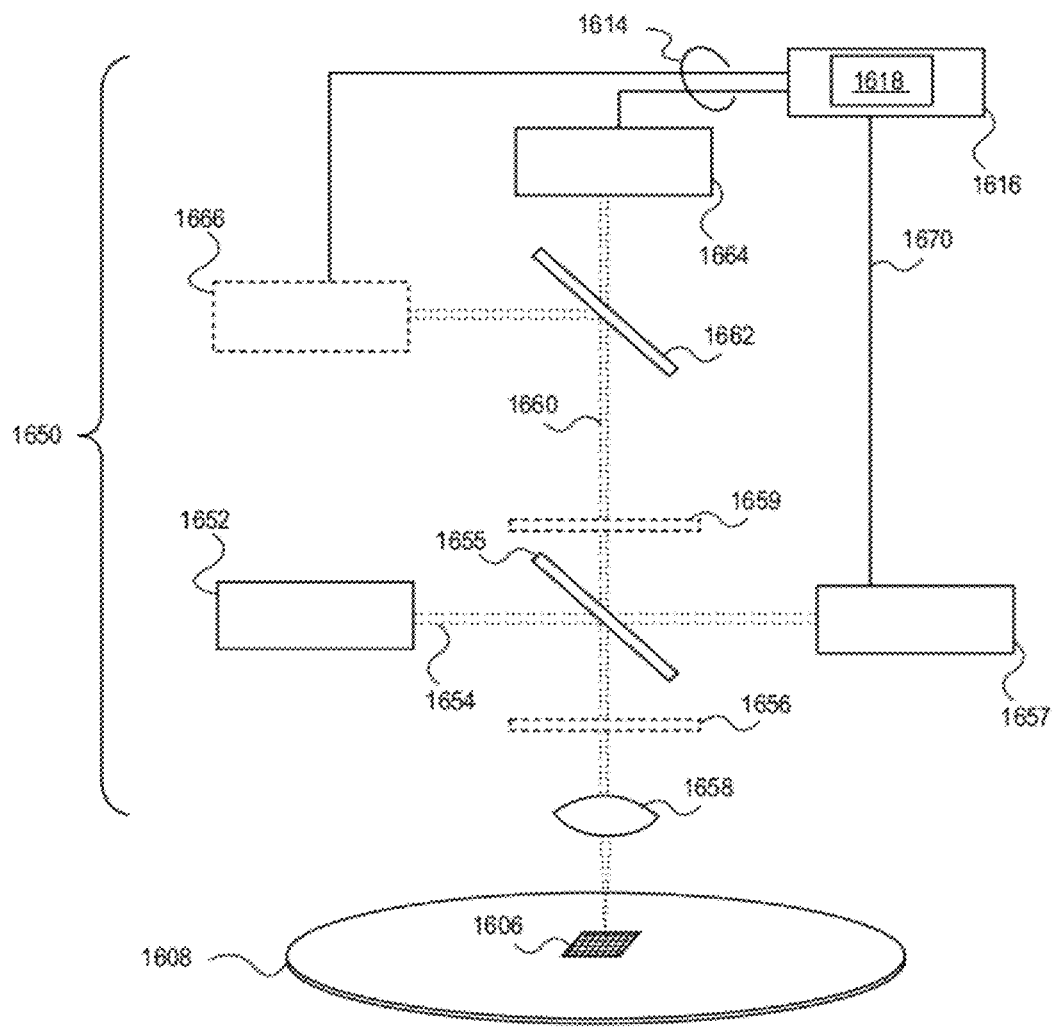

FIG. 16B is an architectural diagram illustrating the utilization of beam-profile reflectometry and/or beam-profile ellipsometry to determine parameters of structures on a semiconductor wafer, in accordance with embodiments of the present invention. The optical metrology system 1650 includes a metrology beam source 1652 generating a polarized metrology beam 1654. Preferably this metrology beam has a narrow bandwidth of 10 nm or less. In some embodiments, the source 1652 is capable of outputting beams of different wavelengths by switching filters or by switching between different lasers or super-bright light emitting diodes. Part of this beam is reflected from the beam splitter 1655 and focused onto the target structure 1606 of a wafer 1608 by objective lens 1658, which has a high numerical aperture (NA), preferably an NA of approximately 0.9 or 0.95. The part of the beam 1654 that is not reflected from the beam splitter is directed to beam intensity monitor 1657. The metrology beam may, optionally, pass through a quarter-wave plate 1656 before the objective lens 1658. After reflection from the target the reflected beam 1660 passes back through the objective lens and is directed to one or more detectors. If optional quarter-wave plate 1656 is present, the beam will pass back through that quarter-wave plate before being transmitted through the beam splitter 1655. After the beam-splitter, the reflected beam 1660 may optionally pass through a quarter-wave plate at location 1659 as an alternative to location 1656. If the quarter-wave plate is present at location 1656, it will modify both the incident and reflected beams. If it is present at location 1659, it will modify only the reflected beam. In some embodiments, no wave plate may be present at either location, or the wave plate may be switched in and out depending on the measurement to be made. It is to be understood that in some embodiments it might be desirable that the wave plate have a retardance substantially different from a quarter wave, i.e. the retardance value might be substantially greater than, or substantially less than, 90°. A polarizer or polarizing beam splitter 1662 directs one polarization state of the reflected beam 1660 to detector 1664, and, optionally, directs a different polarization state to an optional second detector 1666. The detectors 1664 and 1666 might be one-dimensional (line) or two-dimensional (array) detectors. Each element of a detector corresponds to a different combination of AOI and azimuthal angles for the corresponding ray reflected from the target. The diffraction beam data 1614 from the detector(s) is transmitted to the profile application server 1616 along with beam intensity data 1670. The profile application server 1616 may compare the measured diffraction beam data 1614 after normalization or correction by the beam intensity data 1670 against a library 1618 of simulated diffraction beam data representing varying combinations of critical dimensions of the target structure and resolution.

For more detailed descriptions of systems that could measure the diffraction beam data or signals for use with the present invention, see U.S. Pat. No. 6,734,967, entitled FOCUSED BEAM SPECTROSCOPIC ELLIPSOMETRY METHOD AND SYSTEM, filed on Feb. 11, 1999, and U.S. Pat. No. 6,278,519 entitled APPARATUS FOR ANALYZING MULTI-LAYER THIN FILM STACKS ON SEMICONDUCTORS, filed Jan. 29, 1998, both of which are incorporated herein by reference in their entirety. These two patents describe metrology systems that may be configured with multiple measurement subsystems, including one or more of a spectroscopic ellipsometer, a single-wavelength ellipsometer, a broadband reflectometer, a DUV reflectometer, a beam-profile reflectometer, and a beam-profile ellipsometer. These measurement subsystems may be used individually, or in combination, to measure the reflected or diffracted beam from films and patterned structures. The signals collected in these measurements may be analyzed to determine parameters of structures on a semiconductor wafer in accordance with embodiments of the present invention.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 17:
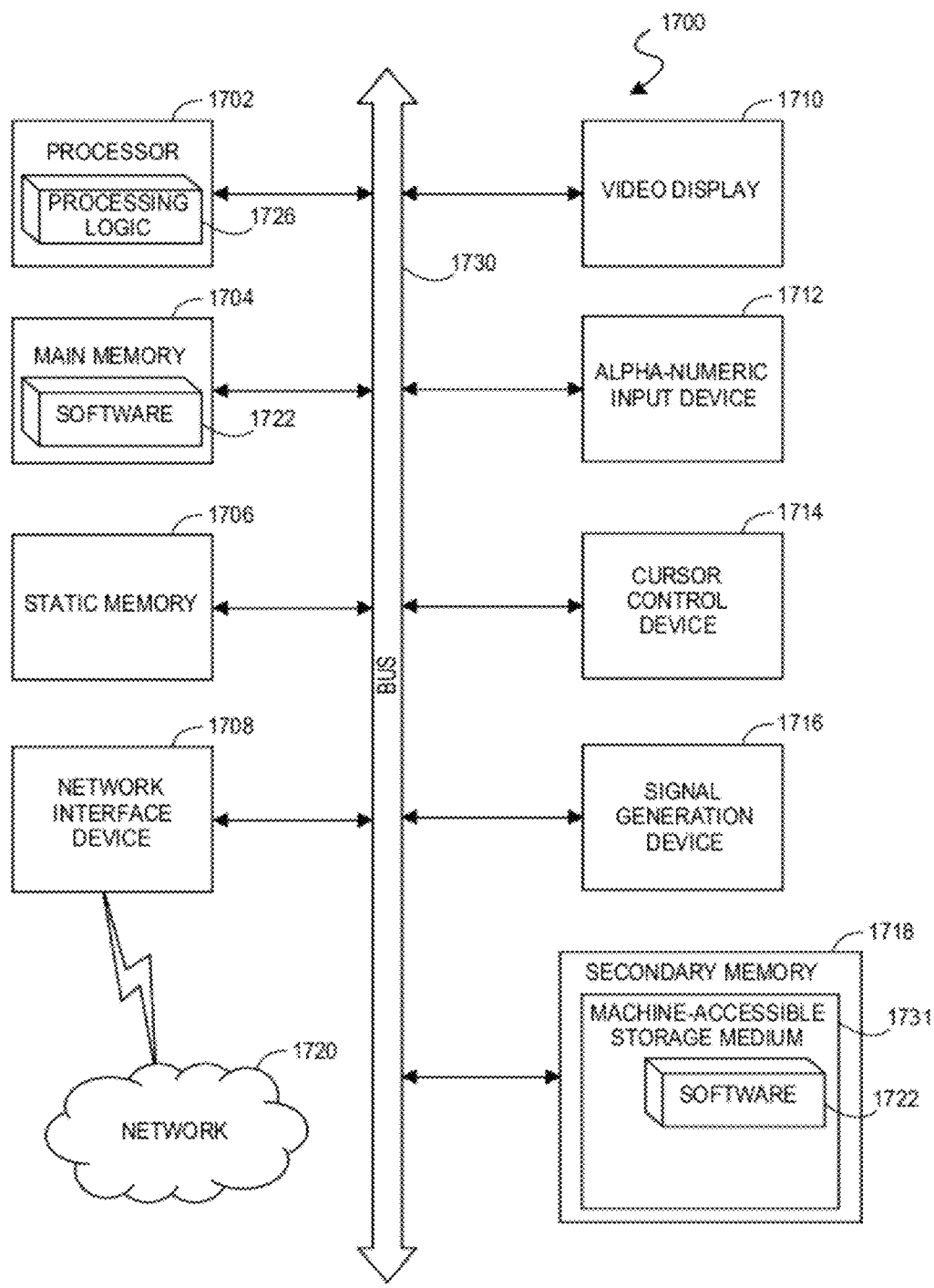
FIG. 17 illustrates a block diagram of an exemplary computer system, in accordance with an embodiment of the present invention.

FIG. 17 illustrates a diagrammatic representation of a machine in the exemplary form of a computer system 1700 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1700 includes a processor 1702, a main memory 1704 (e.g., read-only memory (ROM), flash memory, dynamic random access memory (DRAM)

such as synchronous DRAM (SDRAM) or Rambus DRAM (RDRAM), etc.), a static memory 1706 (e.g., flash memory, static random access memory (SRAM), etc.), and a secondary memory 1718 (e.g., a data storage device), which communicate with each other via a bus 1730.

Processor 1702 represents one or more general-purpose processing devices such as a microprocessor, central processing unit, or the like. More particularly, the processor 1702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1702 may also be one or more special-purpose processing devices such as an application specific integrated circuit (ASIC), a field programmable gate array (FPGA), a digital signal processor (DSP), network processor, or the like. Processor 1702 is configured to execute the processing logic 1726 for performing the operations discussed herein.

The computer system 1700 may further include a network interface device 1708. The computer system 1700 also may include a video display unit 1710 (e.g., a liquid crystal display (LCD) or a cathode ray tube (CRT)), an alphanumeric input device 1712 (e.g., a keyboard), a cursor control device 1714 (e.g., a mouse), and a signal generation device 1716 (e.g., a speaker).

The secondary memory 1718 may include a machine-accessible storage medium (or more specifically a computer-readable storage medium) 1731 on which is stored one or more sets of instructions (e.g., software 1722) embodying any one or more of the methodologies or functions described herein. The software 1722 may also reside, completely or at least partially, within the main memory 1704 and/or within the processor 1702 during execution thereof by the computer system 1700, the main memory 1704 and the processor 1702 also constituting machine-readable storage media. The software 1722 may further be transmitted or received over a network 1720 via the network interface device 1708.

While the machine-accessible storage medium 1731 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a machine-accessible storage medium has instructions stored thereon which cause a data processing system to perform a method of optimizing optical parametric models for structural analysis using OCD metrology. The method includes determining a first optical model fit for a parameter of a structure. The first optical model fit is based on a domain of wavelengths for a first model of the structure. A first near optical field response is determined for a first wavelength of the domain of wavelengths and a second near optical field response is determined for a second, different wavelength of the domain of wavelengths. The first and second near optical field responses are compared to locate a common region of high optical field intensity for the parameter of the structure. The first model of the structure is modified to provide a second, different model of the structure. A second, different optical model fit is determined for the parameter of the structure based on the second model of the structure.

In an embodiment, determining the first optical model fit for the parameter of the structure includes determining the first optical model fit for a shape of the structure or for a film thickness within the structure.

In an embodiment, determining the first and second near optical field responses includes selecting the first and second wavelengths from a region of low correlation of the first optical model fit. In one such embodiment, selecting the first and second wavelengths from a region of low correlation of the first optical model fit includes selecting an angle of incidence for the first wavelength and using the angle of incidence for the second wavelength.

In an embodiment, determining the first and second near optical field responses includes generating a pair of contour plots, and comparing the first and second near optical field responses includes comparing the pair of contour plots.

In an embodiment, the method further includes determining a third, different optical model fit for the parameter of the structure based on a third model of the structure.

In another embodiment, a machine-accessible storage medium has instructions stored thereon which cause a data processing system to perform a method of optimizing optical parametric models for three-dimensional structural analysis using OCD metrology. The method includes determining a first optical model fit for a parameter of a three-dimensional structure. The first optical model fit is based on a domain of wavelengths for a first model of the three-dimensional structure. A first near optical field response is determined for a first wavelength of the domain of wavelengths at a plurality of azimuth angles. A second near optical field response is determined for a second, different wavelength of the domain of wavelengths at one of the plurality of azimuth angles. The first and second near optical field responses are compared to locate a common region of high optical field intensity for the parameter of the three-dimensional structure. The first model of the three-dimensional structure is modified to provide a second, different model of the three-dimensional structure. A second, different optical model fit for the parameter of the three-dimensional structure is determined based on the second model of the three-dimensional structure.

In an embodiment, determining the first optical model fit for the parameter of the three-dimensional structure includes determining the first optical model fit for a shape of the three-dimensional structure or for a film thickness within the three-dimensional structure.

In an embodiment, determining the first and second near optical field responses includes selecting the first and second wavelengths from a region of low correlation of the first optical model fit. In one such embodiment, selecting the first and second wavelengths from a region of low correlation of the first optical model fit includes selecting an angle of incidence for the first wavelength and using the angle of incidence for the second wavelength.

In an embodiment, determining the first and second near optical field responses includes generating a pair of contour plots, and comparing the first and second near optical field responses includes comparing the pair of contour plots.

In an embodiment, the method further includes determining a third, different optical model fit for the parameter of the three-dimensional structure based on a third model of the three-dimensional structure.

It is to be understood that the above methodologies may be applied under a variety of circumstances within the spirit and scope of embodiments of the present invention. For example, in an embodiment, measurements described above are performed with or without the presence of background light. In an embodiment, a method described above is performed in a semiconductor, solar, light-emitting diode (LED), or a related fabrication process. In an embodiment, a method described above is used in a stand-alone or an integrated metrology tool.

Figure 18:
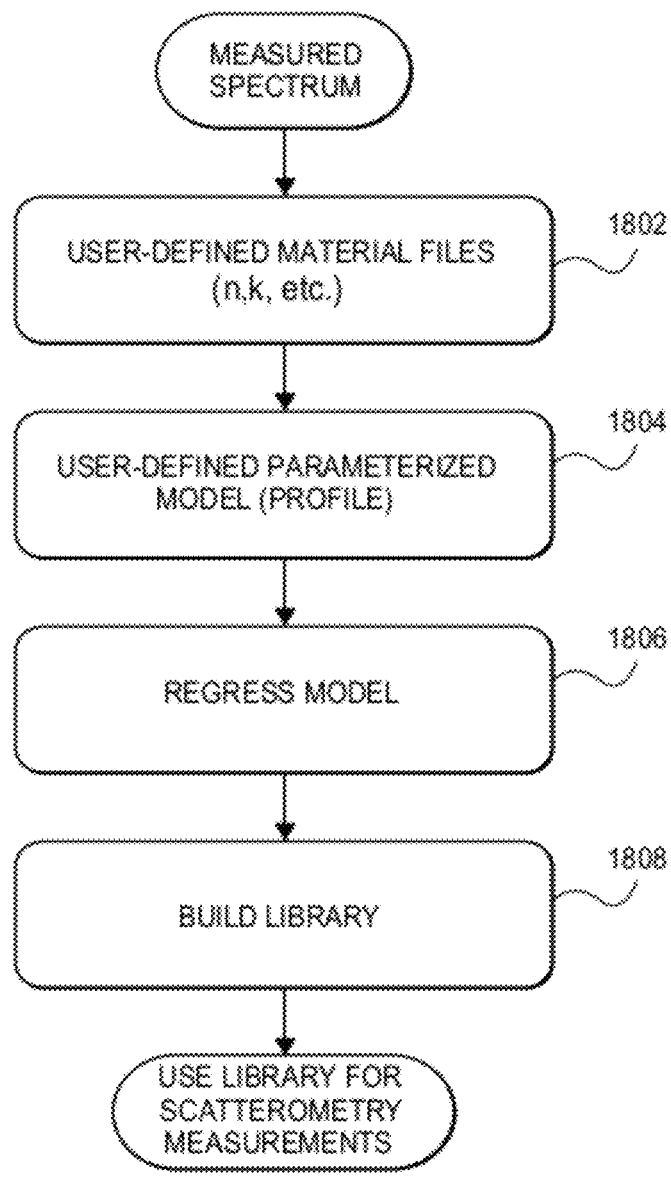
FIG. 18 is a flowchart representing operations in a method for a building parameterized model and a spectral library beginning with sample spectra, in accordance with an embodiment of the present invention.

Analysis of measured spectra generally involves comparing the measured sample spectra to simulated spectra to deduce parameter values of a model that best describe the measured sample. FIG. 18 is a flowchart 1800 representing operations in a method for a building parameterized model and a spectral library beginning with sample spectra (e.g., originating from one or more workpieces), in accordance with an embodiment of the present invention.

At operation 1802, a set of material files are defined by a user to specify characteristics (e.g., refractive index or n, k values) of the material(s) from which the measured sample feature is formed.

At operation 1804, a scatterometry user defines a nominal model of the expected sample structure by selecting one or more of the material files to assemble a stack of materials corresponding to those present in the periodic grating features to be measured. Such a user-defined model may be further parameterized through definition of nominal values of model parameters, such as thicknesses, critical dimension (CD), sidewall angle (SWA), height (HT), edge roughness, corner rounding radius, etc. which characterize the shape of the feature being measured. Depending on whether a two-dimensional model (i.e., a profile) or three-dimensional model is defined, it is not uncommon to have 30-50, or more, such model parameters.

From a parameterized model, simulated spectra for a given set of grating parameter values may be computed using rigorous diffraction modeling algorithms, such as Rigorous Coupled Wave Analysis (RCWA). Regression analysis is then performed at operation 1806 until the parameterized model converges on a set of parameter values characterizing a final profile model (for two-dimensional) that corresponds to a simulated spectrum which matches the measured diffraction spectra to a predefined matching criterion. The final profile model associated with the matching simulated diffraction signal is presumed to represent the actual profile of the structure from which the model was generated.

The matching simulated spectra and/or associated optimized profile model can then be utilized at operation 1808 to generate a library of simulated diffraction spectra by perturbing the values of the parameterized final profile model. The resulting library of simulated diffraction spectra may then be employed by a scatterometry measurement system operating in a production environment to determine whether subsequently measured grating structures have been fabricated according to specifications. Library generation 1808 may include a machine learning system, such as a neural network, generating simulated spectral information for each of a number of profiles, each profile including a set of one or more modeled profile parameters. In order to generate the library, the machine learning system itself may have to undergo some training based on a training data set of spectral information. Such training may be computationally intensive and/or may have to be repeated for different models and/or profile parameter domains. Considerable inefficiency in the computational load of generating a library may be introduced by a user's decisions regarding the size of a training data set. For example, selection of an overly large training data set may result in unnecessary computations for training while training with a training data set of insufficient size may necessitate a retraining to generate a library.

For some applications it may be unnecessary to build a library. After the parametric model of the structure has been created and optimized, a regression analysis similar to that described above may be used in real time to determine the best fitting parameter values for each target as the diffraction beam data are collected. If the structure is relatively simple (for example a 2D structure), or if only a small number of parameters need to be measured, regression may be fast enough even though it may be slower than using a library. In other cases, the extra flexibility of using regression may justify some increase in measurement time over using a library. For a more detailed description of methods and systems that are capable of real-time regression of OCD data for use with the present invention, see U.S. Pat. No. 7,031,848, entitled REAL TIME ANALYSIS OF PERIODIC STRUCTURES ON SEMICONDUCTORS, filed on Jul. 8, 2005, which is incorporated herein by reference in its entirety.

Figure 19:
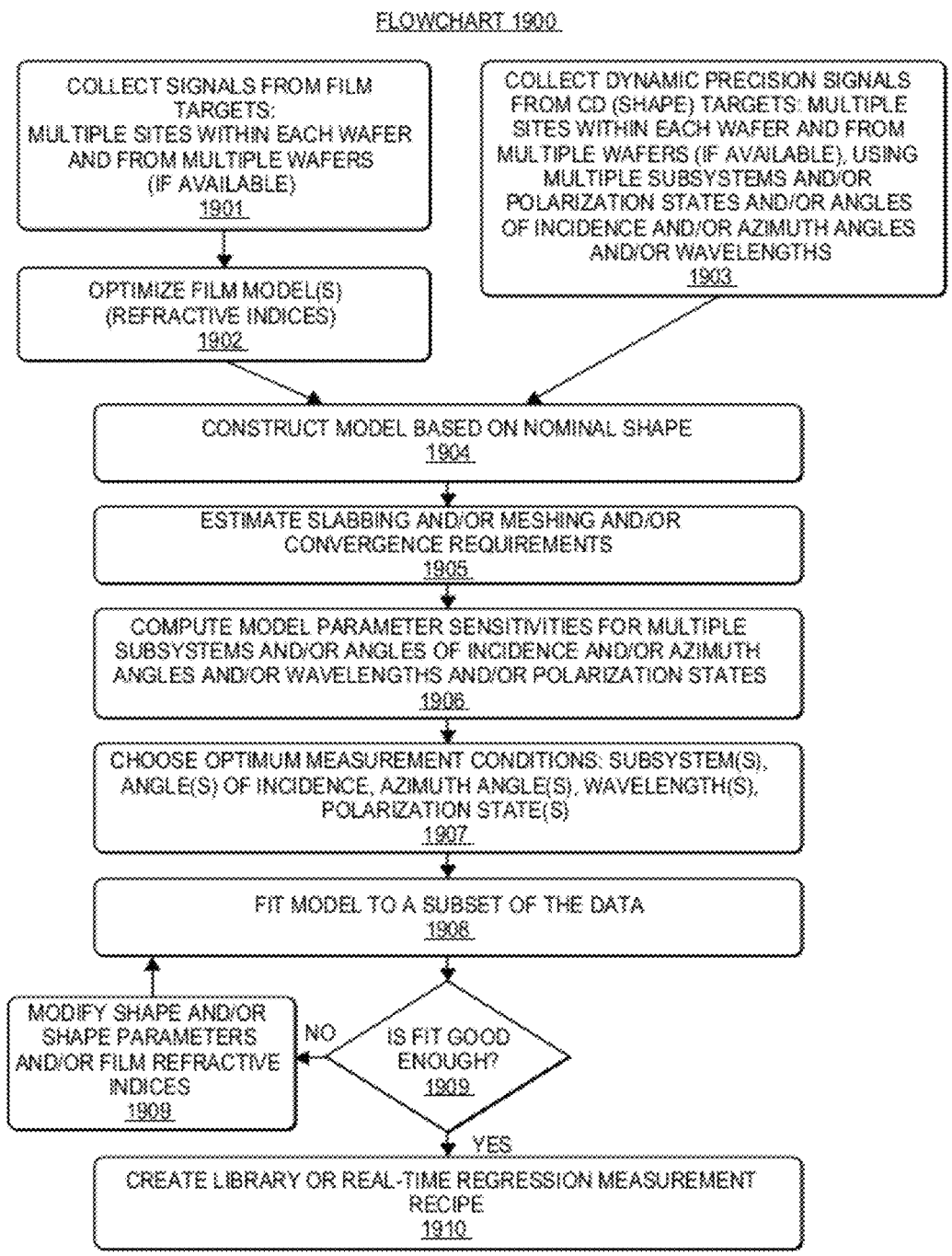
FIG. 19 is an illustrative flowchart representing operations in a method for building a parameterized model of a structure beginning with signals collected at multiple wavelengths and/or angles and/or polarization states in accordance with an embodiment of this invention. Various methods of embodiments of the present invention may be used at one or more operations in this flowchart.

FIG. 19 depicts a flowchart 1900 representing operations in a method of optimizing optical parametric models for structural analysis using OCD metrology, in accordance with an embodiment of the present invention. Not every operation shown is required during the optimization of every parametric model. Some models may be optimized using a subset of the operations shown. It should further be understood that some of these operations may be performed in a different sequence or that additional operations may be inserted into the sequence without departing from the scope of the present invention.

Usually the development of a parametric model starts with collect of signal data (which might be spectroscopic data or angle resolved data or a combination of the two) on film targets (1901) and on patterned (CD) targets (1903). It is generally useful to make multiple measurements of some or all of the patterned targets so that the repeatability of the parameter determination process can be assessed from the same measurement data after a parametric model has been created. The collection of repeated signal data from the same targets does not always need to be done, or might be postponed to a later time. The film and patterned targets may be on the same wafer(s), or the film targets may be on different wafers that have been processed through substantially similar film deposition operations.

Referring to operation 1902, the film signal data may be used to generate film models (refractive indices and coefficients of extinction). In cases where the films have been previously characterized or are known from prior information, operations 1901 and 1902 may be omitted.

Referring to operation 1904, an initial parametric model is constructed using the nominal shape information (and any existing prior information relating to the shapes) and the film models from operation 1902 or from prior knowledge or characterization.

All electromagnetic algorithms for calculating the optical response of structures require discretization of the structure. RCWA, as explained above, requires that the structure be divided into slabs, and then the fields in each slab are expressed as Fourier series. Finite element and finite difference techniques perform calculations on a mesh, or grid, of points. Operation 1905 involves selecting the number and location of slabs, the number of terms and/or orders to retain in any series expansion and/or selecting the mesh points as appropriate. This process may be completely automated or may require manual input of some of the information. Operation 1905 involves a tradeoff between calculation accuracy (convergence) and computation time, and depends, among other factors, on the shape of the structure and refractive indices and coefficients of extinction of the materials involved.

Operation 1906 involves determining the change in signal for small changes in each of the parameters of the parametric model of the structure. Usually the signal change is computed for one or more of the available measurement subsystems (e.g. SE, BPR, BPE, UVR) and/or for different operating modes of those subsystems, such as different azimuth angles, different wavelengths or different polarization states. The change in signal is compared with the expected noise on the signal in order to determine the sensitivity to measure each parameter. One or more of the embodiments of the present invention can usefully be employed in this operation in order to determine which combination(s) of angles, wavelengths and polarization states correspond to strong near optical fields in regions of interest and, therefore likely have good sensitivity to the model parameters corresponding to those regions. The results of operation 1906 can be used to decide which measurement subsystem(s) and operating mode(s) are best suited for making the measurement and which parameters of the parametric model should be kept fixed and which should be allowed to vary.

Operation 1908 involves testing the parametric model by fitting it to some or all of the signal data collection in operation 1903. Typically it is preferred only to use a subset of the data in the interests of saving time at this point in the process. The quality of the fit is assessed by looking at the value of chi-squared or other metric of the goodness of the fit (operation 1909). If the quality of the fit is good enough, then the parametric model can be used to develop the library and measurement recipe used to make scatterometry measurements of wafers in production (operation 1910, which is explained in more detail in FIGS. 20 and 21).

If the quality of the fit is not good enough, e.g. the chi-squared value for the best fitting set of parameters is too high, then the parametric model needs to be modified as shown at operation 1909. One or more of the embodiments of the present invention can be employed to determine which additional parameters of the parametric model should be allowed to vary or which additional parameters should be held fixed or which parts of the shape should be changed or parameterized differently based on the information about where, and under what conditions, the near optical fields are strong and weak. Embodiments of the invention can also help determine which material refractive index and/or coefficient of extinction might usefully be modified to improve the quality of the fit. Embodiments of the present invention can also provide information to determine whether changes should be made to the measurement subsystem(s) and/or operating mode(s) to see if the quality of the fit can be improved. Although FIG. 19 shows operation 1909 looping back to operation 1908, it should be understood that the loop could be made back to any of the preceding operations.

Figure 20:
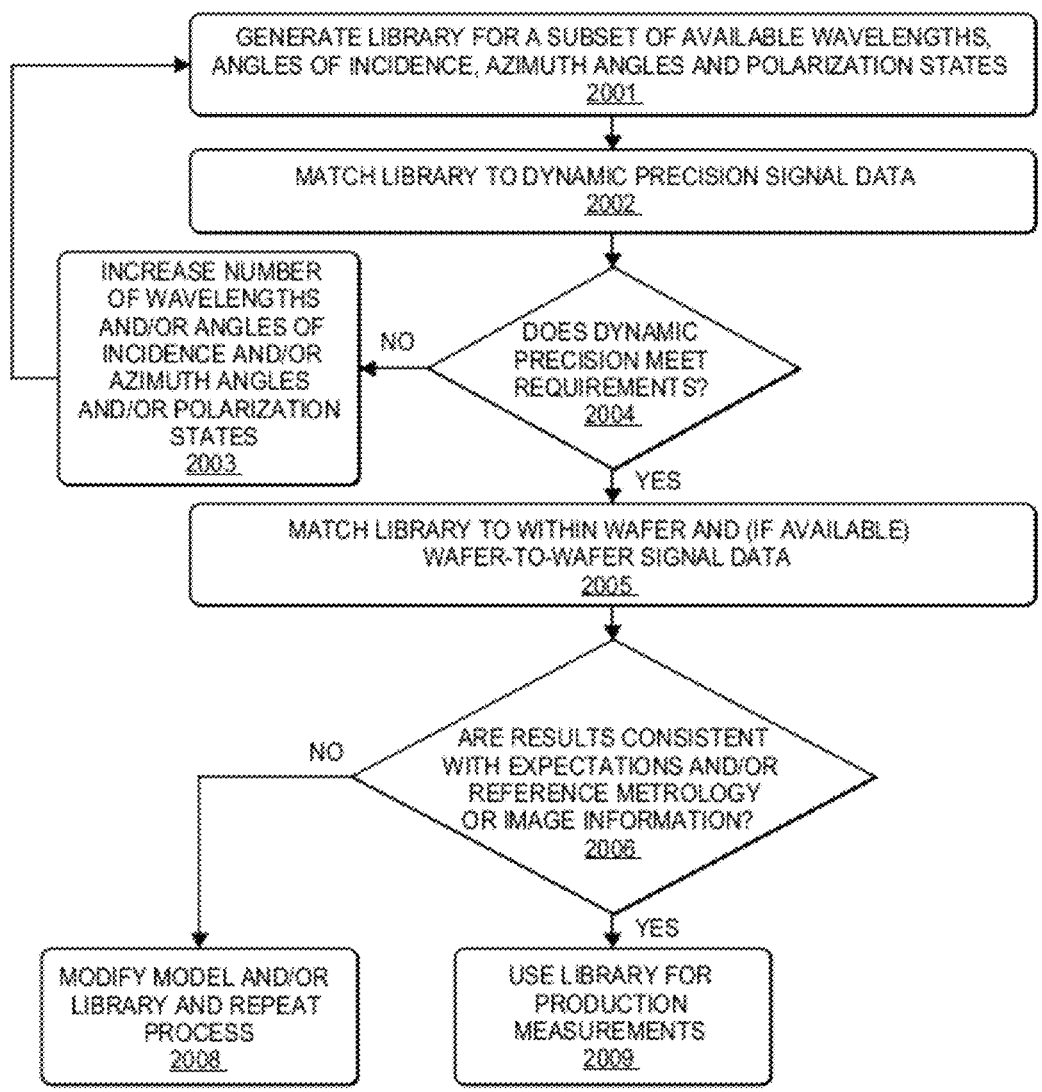
FIG. 20 is an illustrative flowchart representing operations in a method for building a library for making production measurements of a structure in accordance with an embodiment of this invention. This library may be generated from a parameterized model developed using one or more of the methods of the embodiments of the present invention. Various methods of embodiments of the present invention may also be used at one or more operations in this flowchart.

FIG. 20 depicts a flowchart 2000 representing operations in a method of constructing and optimizing a library using an optical parametric model, in accordance with an embodiment of the present invention. Not every operation shown is always required. Some libraries may be optimized using a subset of the operations shown. It should be understood that some of these operations may be performed in a different sequence or that additional operations may be inserted into the sequence without departing from the scope of the present invention.

Referring to operation 2001, a library is created using a parametric model. That parametric model may have been created and optimized using a process such as those illustrated in FIGS. 3, 12 and 19. The library is preferably created for a subset of the available wavelengths and angles in order to keep the library size small and to speed the library match or search. The library is then used to match dynamic precision signal data as shown at operation 2002 and hence determine the precision or repeatability of the measurement using that library. If the resulting precision does not meet requirements (operation 2004), then the number of wavelengths and/or angles and/or polarization states used needs to be increased as shown at operation 2003 and the process repeated. It is to be understood that if the dynamic precision is significantly better than required, it may be desirable to reduce the number of wavelengths and/or angles and/or polarization states in order to make a smaller, faster library. Embodiments of the present invention can be used to determine which additional wavelengths, angles or incidence, azimuth angles and/or polarizations states to include in the library based on the strength of near optical fields in regions near model parameters with measurement precisions not meeting requirements.

When the library has been optimized for precision, any additional data that is available can be matched using that library as shown at operation 2005. The results from the larger set of data can be compared with reference data such as cross-section electron micrographs and also checked for consistency between wafers (for example, two wafers processed on the same equipment will usually show similar across-wafer variations) as shown at operation 2006. If the results meet expectations, then the library is ready for scatterometry measurements of production wafers (operation 2009). If the results do not meet expectations, then the library and/or parametric model need to be updated and the resulting new library retested (operation 2008). One or more embodiments of the present invention can used to determine what changes have to be made to the library or parametric model to improve the results. The near optical fields can identify the combinations of wavelengths, angles and polarization states that give the best sensitivity to parameters of interest or which can reduce correlations between different parameters.

Figure 21:
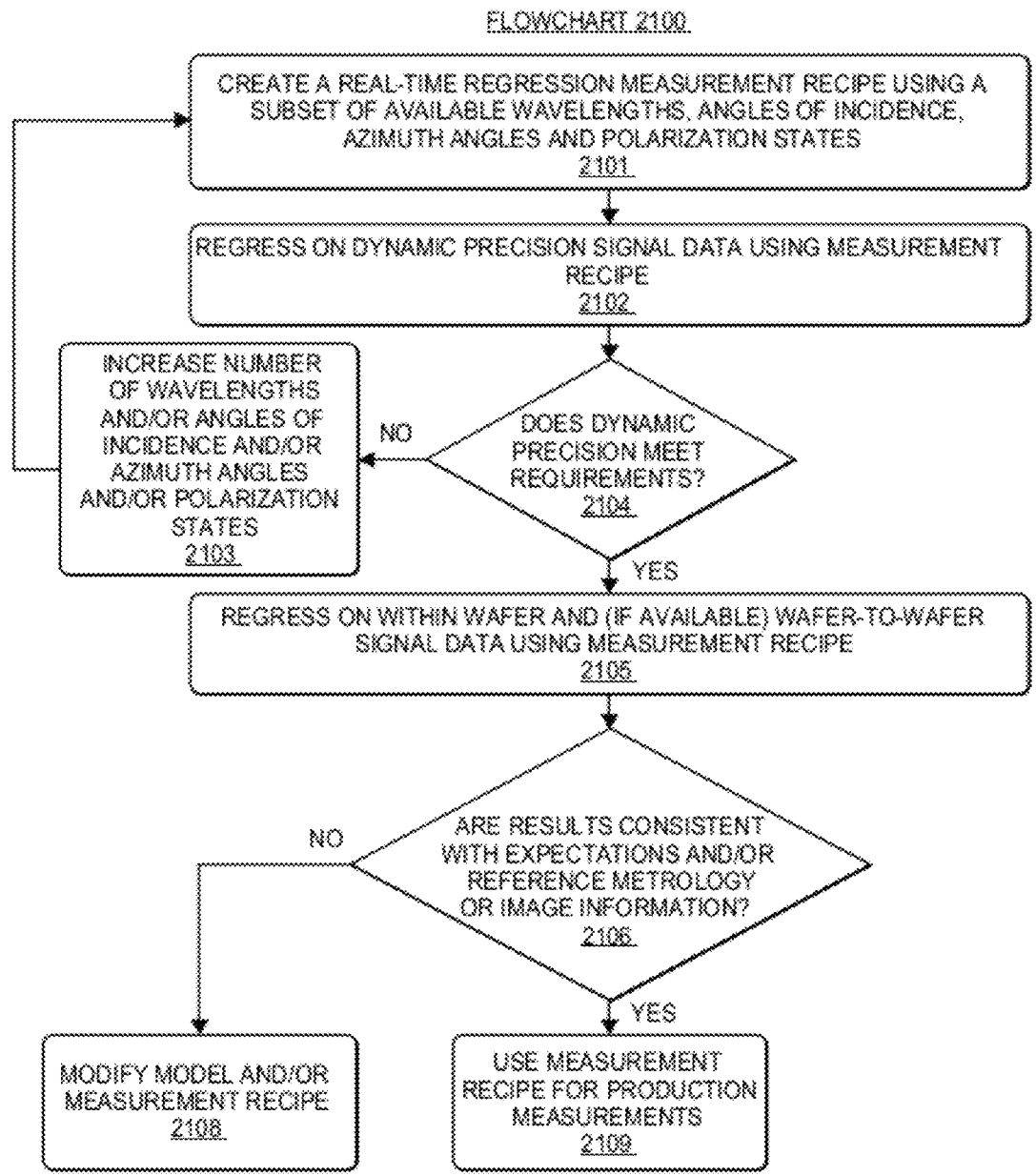
FIG. 21 is an illustrative flowchart representing operations in a method for building a real-time regression measurement recipe for making production measurements of a structure in accordance with an embodiment of this invention. The recipe may incorporate a parameterized model developed using one or more of the methods of the embodiments of the present invention. Various methods of the embodiments of the present invention may also be used at one or more operations in this flowchart.

FIG. 21 depicts a flowchart 2100 representing operations in a method of constructing and optimizing a real-time regression measurement recipe using an optical parametric model, in accordance with an embodiment of the present invention. Not every operation shown is always required. Some real-time regression measurement recipes may be optimized using a subset of the operations shown. It should be understood that some of these operations may be performed in a different sequence or that additional operations may be inserted into the sequence without departing from the scope of the present invention.

Referring to operation 2101, a real-time regression measurement recipe is created using a parametric model. That parametric model may have been created and optimized using a process such as those illustrated in FIGS. 3, 12 and 19. The recipe is preferably created for a subset of the available wavelengths and angles in order to keep the computation time as short as possible. The recipe is then used to regress on the dynamic precision signal data as shown at operation 2102 and hence determine the precision or repeatability of the measurement using that library. If the resulting precision does not meet requirements (operation 2104), then the number of wavelengths and/or angles and/or polarization states used needs to be increased as shown at operation 2103 and the process repeated. It is to be understood that if the dynamic precision is significantly better than required, it may be desirable to reduce the number of wavelengths and/or angles and/or polarization states in order to make a faster recipe. Embodiments of the present invention can be used to determine which additional wavelengths, angles or incidence, azimuth angles and/or polarizations states to include in the recipe based on the strength of near optical fields in regions near model parameters with measurement precisions not meeting requirements.

When the recipe has been optimized for precision, any additional data that is available can be regressed using that recipe as shown at operation 2105. The results from the larger set of data can be compared with reference data such as cross-section electron micrographs and also checked for consistency between wafers (for example, two wafers processed on the same equipment will usually show similar across-wafer variations) as shown at operation 2106. If the results meet expectations, then the recipe is ready for scatterometry measurements of production wafers (operation 2109). If the results do not meet expectations, then the recipe and/or parametric model need to be updated and the resulting new recipe retested (operation 2108). One or more embodiments of the present invention can used to determine what changes have to be made to the recipe or parametric model to improve the results. The near optical fields can identify the combinations of wavelengths, angles and polarization states that give the best sensitivity to parameters of interest or which can reduce correlations between different parameters.

As illustrated in the above examples, the process of developing parametric models and libraries and real-time regression recipes that use those parametric models is often an iterative process. The present invention can significantly reduce the number of iterations required to arrive at parametric model and the libraries or real-time regression recipe using that model as compare with a trial-end-error approach. The present invention also significantly improves the measurement performance of the resulting parametric models, libraries and real-time regression recipes since the model parameters, wavelengths, angles of incidence, azimuthal angles and polarization states can all be chosen based on optimizing sensitivity and reducing correlations.

It is also to be understood that embodiments of the present invention also include the use of the techniques related to machine learning systems such as neural networks and support vector machines to generate simulated diffraction signals.

Thus, methods for optimizing optical parametric models for structural analysis using OCD metrology have been disclosed. In accordance with an embodiment of the present invention, a method includes determining a first optical model fit for a parameter of a structure, the first optical model fit based on a domain of wavelengths for a first model of the structure. The method also includes determining a first near optical field response for a first wavelength of the domain of wavelengths and a second near optical field response for a second, different wavelength of the domain of wavelengths. The method also includes comparing the first and second near optical field responses to locate a common region of high optical field intensity for the parameter of the structure. The method also includes modifying the first model of the structure to provide a second, different model of the structure. The method also includes determining a second, different optical model fit for the parameter of the structure based on the second model of the structure. In one embodiment, determining the first optical model fit for the parameter of the structure includes determining the first optical model fit for a shape of the structure or for a film thickness within the structure. In one embodiment, determining the first and second near optical field responses includes selecting the first and second wavelengths from a region of low correlation of the first optical model fit.

What is claimed is:

1. A method of optimizing optical parametric models for structural analysis using optical critical dimension (OCD) metrology with an optical metrology system, the optical metrology system including a processor coupled with a memory and an optical metrology tool, the method performed by the optical metrology system comprising:
    measuring values of far field diffraction signals for a structure, the measurement being performed by the optical metrology tool of the optical metrology system;
    determining a first optical model fit for a parameter of the structure, the first optical model fit based on a domain of quantities for a first model of the structure;
    determining a first near optical field response for a first quantity of the domain of quantities and a second near optical field response for a second, different quantity of the domain of quantities, wherein the domain of quantities is a domain of wavelengths, the first quantity being a first wavelength and the second quantity being a second wavelength, and wherein determining the first and second near optical field responses comprises:
        identifying a region of low correlation of the first optical model fit with measured values for the structure, and selecting the first and second wavelengths from the region of low correlation of the first optical model fit;
    comparing the first and second near optical field responses to locate a common region of high near optical field intensity for the parameter of the structure;
    modifying the first model of the structure based at least in part on the common region of high near optical field intensity to provide a second, different model of the structure; and determining a second, different optical model fit for the parameter of the structure based on the second model of the structure.

2. The method of claim 1, wherein determining the first optical model fit for the parameter of the structure comprises determining the first optical model fit for a shape of the structure or for a film thickness within the structure.

3. The method of claim 1, wherein selecting the first and second wavelengths from the region of low correlation of the first optical model fit comprises selecting an angle of incidence for the first wavelength and using the angle of incidence for the second wavelength.

4. The method of claim 1, wherein determining the first and second near optical field responses comprises generating a pair of contour plots, and wherein comparing the first and second near optical field responses comprises comparing the pair of contour plots.

5. The method of claim 1, further comprising: determining a third, different optical model fit for the parameter of the structure based on a third model of the structure.

6. The method of claim 1, further comprising:
    computing a near optical field for the structure.

7. A method of optimizing optical parametric models for three-dimensional structural analysis using optical critical dimension (OCD) metrology with an optical metrology system, the optical metrology system including a processor coupled with a memory and an optical metrology tool, the method performed by the optical metrology system comprising:
    measuring values of far field diffraction signals for a three-dimensional structure, the measurement being performed by the optical metrology tool of the optical metrology system;
    determining a first optical model fit for a parameter of the three-dimensional structure, the first optical model fit based on a domain of wavelengths for a first model of the three-dimensional structure;

determining a first near optical field response for a first wavelength of the domain of wavelengths at a plurality of azimuth angles;

determining a second near optical field response for a second, different wavelength of the domain of wavelengths at one of the plurality of azimuth angles, wherein determining the first and second near optical field responses comprises:

identifying a region of low correlation of the first optical model fit with measured values for the structure, and selecting the first and second wavelengths from the region of low correlation of the first optical model fit;

comparing the first and second near optical field responses to locate a common region of high near optical field intensity for the parameter of the three-dimensional structure;

modifying the first model of the three-dimensional structure based at least in part on the common region of high near optical field intensity to provide a second, different model of the three-dimensional structure; and determining a second, different optical model fit for the parameter of the three-dimensional structure based on the second model of the three-dimensional structure.

8. The method of claim 7, wherein determining the first optical model fit for the parameter of the three-dimensional structure comprises determining the first optical model fit for a shape of the three-dimensional structure or for a film thickness within the three-dimensional structure.

9. The method of claim 7, wherein selecting the first and second wavelengths from the region of low correlation of the first optical model fit comprises selecting an angle of incidence for the first wavelength and using the angle of incidence for the second wavelength.

10. The method of claim 7, wherein determining the first and second near optical field responses comprises generating a pair of contour plots, and wherein comparing the first and second near optical field responses comprises comparing the pair of contour plots.

11. The method of claim 7, further comprising: determining a third, different optical model fit for the parameter of the three-dimensional structure based on a third model of the three-dimensional structure.

12. The method of claim 7, further comprising:
computing a near optical field for the three-dimensional structure.

13. A non-transitory machine-accessible storage medium having instructions stored thereon which cause a data processing system to perform a method of optimizing optical parametric models for structural analysis using optical critical dimension (OCD) metrology with an optical metrology system, the optical metrology system including a processor coupled with a memory and an optical metrology tool, the method comprising:

measuring values of far field diffraction signals for a structure with the optical metrology tool of the optical metrology system;

determining a first optical model fit for a parameter of the structure, the first optical model fit based on a domain of quantities for a first model of the structure;

determining a first near optical field response for a first quantity of the domain of quantities and a second near optical field response for a second, different quantity of the domain of quantities, wherein the domain of quantities is the first quantity being a first wavelength and the second quantity being a second wavelength, and wherein determining the first and second near optical field responses comprises:

identifying a region of low correlation of the first optical model fit with measured values for the structure, and selecting the first and second wavelengths from the region of low correlation of the first optical model fit; comparing the first and second near optical field responses to locate a common region of high near optical field intensity for the parameter of the structure;

modifying the first model of the structure based at least in part on the common region of high near optical field intensity to provide a second, different model of the structure; and determining a second, different optical model fit for the parameter of the structure based on the second model of the structure.

14. The storage medium as in claim 13, wherein determining the first optical model fit for the parameter of the structure comprises determining the first optical model fit for a shape of the structure or for a film thickness within the structure.

15. The storage medium as in claim 13, wherein selecting the first and second wavelengths from the region of low correlation of the first optical model fit comprises selecting an angle of incidence for the first wavelength and using the angle of incidence for the second wavelength.

16. The storage medium as in claim 13, wherein determining the first and second near optical field responses comprises generating a pair of contour plots, and wherein comparing the first and second near optical field responses comprises comparing the pair of contour plots.

17. The storage medium as in claim 13, the method further comprising: determining a third, different optical model fit for the parameter of the structure based on a third model of the structure.

18. The storage medium as in claim 13, wherein the method further comprises: computing a near optical field for the structure.

19. A non-transitory machine-accessible storage medium having instructions stored thereon which cause a data processing system to perform a method of optimizing optical parametric models for three-dimensional structural analysis using optical critical dimension (OCD) metrology with an optical metrology system, the method comprising:

measuring values of far field diffraction signals for a three-dimensional structure with an optical metrology tool of the optical metrology system;

determining a first optical model fit for a parameter of the three-dimensional structure, the first optical model fit based on a domain of wavelengths for a first model of the three-dimensional structure;

determining a first near optical field response for a first wavelength of the domain of wavelengths at a plurality of azimuth angles;

determining a second near optical field response for a second, different wavelength of the domain of wavelengths at one of the plurality of azimuth angles, wherein determining the first and second near optical field responses comprises:

identifying a region of low correlation of the first optical model fit with measured values for the three-dimensional structure, and selecting the first and second wavelengths from the region of low correlation of the first optical model fit;

comparing the first and second near optical field responses to locate a common region of high near optical field intensity for the parameter of the three-dimensional structure;

modifying the first model of the three-dimensional structure based at least in part on the common region of high near optical field intensity to provide a second, different model of the three-dimensional structure; and determining a second, different optical model fit for the parameter of the three-dimensional structure based on the second model of the three-dimensional structure.

20. The storage medium as in claim 17, wherein determining the first optical model fit for the parameter of the three-dimensional structure comprises determining the first optical model fit for a shape of the three-dimensional structure or for a film thickness within the three-dimensional structure.

21. The storage medium as in claim 19, wherein selecting the first and second wavelengths from the region of low correlation of the first optical model fit comprises selecting an angle of incidence for the first wavelength and using the angle of incidence for the second wavelength.

22. The storage medium as in claim 19, wherein determining the first and second near optical field responses comprises generating a pair of contour plots, and wherein comparing the first and second near optical field responses comprises comparing the pair of contour plots.

23. The storage medium as in claim 19, the method further comprising: determining a third, different optical model fit for the parameter of the three-dimensional structure based on a third model of the three-dimensional structure.

24. The storage medium as in claim 19, wherein the method further comprises: computing a near optical field for the three-dimensional structure.

* * * * *